(12) United States Patent
Rauwald et al.

(10) Patent No.: US 8,378,059 B2
(45) Date of Patent: Feb. 19, 2013

(54) SUPRAMOLECULAR HANDCUFFS IN POLYMERIC ARCHITECTURE

(75) Inventors: Urs Rauwald, Cambridge (GB); Oren Alexander Scherman, Cambridge (GB)

(73) Assignee: Cambridge Enterprise Ltd., Cambridge (GB)

( * ) Notice: Subject to any disclaimer, the term of this patent is extended or adjusted under 35 U.S.C. 154(b) by 39 days.

(21) Appl. No.: 12/734,925

(22) PCT Filed: Dec. 4, 2008

(86) PCT No.: PCT/GB2008/004016
§ 371 (c)(1),
(2), (4) Date: Jun. 3, 2010

(87) PCT Pub. No.: WO2009/071899
PCT Pub. Date: Jun. 11, 2009

(65) Prior Publication Data
US 2010/0247477 A1    Sep. 30, 2010

(30) Foreign Application Priority Data
Dec. 4, 2007   (GB) .................................. 0723714.2

(51) Int. Cl.
*A61K 31/787*  (2006.01)
*C08G 73/00*   (2006.01)
*C08G 79/00*   (2006.01)

(52) U.S. Cl. ............................. 528/367; 424/78.3; 528/9

(58) Field of Classification Search .................. None
See application file for complete search history.

(56) References Cited

U.S. PATENT DOCUMENTS

| 7,060,498 B1 * | 6/2006 | Wang ............................ 435/455 |
| 2002/0133003 A1 | 9/2002 | Kim et al. |
| 2004/0247680 A1 * | 12/2004 | Farokhzad et al. ........... 424/486 |
| 2006/0154254 A1 | 7/2006 | Kim et al. |
| 2006/0292570 A1 * | 12/2006 | Keinan ............................. 435/6 |

FOREIGN PATENT DOCUMENTS

| JP | A-2007-211060 | 8/2007 |
| WO | WO 2005/023816 A2 | 3/2005 |
| WO | WO 2007/046575 A1 | 4/2007 |
| WO | WO 2007/106144 A1 | 9/2007 |
| WO | WO 2008/096360 A2 | 8/2008 |

OTHER PUBLICATIONS

Wang, Angew. Chem. Int. ed., 45, 2006.*
Lim, Bioconjugate Chem, 13, 2002.*
Glossary, Drug-Discovery-and-Development, 2012, p. 23.*

(Continued)

*Primary Examiner* — Susan Tran
*Assistant Examiner* — William Craigo
(74) *Attorney, Agent, or Firm* — Oliff & Berridge, PLC

(57) ABSTRACT

This invention pertains generally to supramolecular polymers comprising a polymeric molecule linked to a first CB[8] guest molecule and an attachment compound linked to a second CB[8] guest molecule, wherein the first and second CB[8] guest molecules form a ternary host-guest complex with a CB[8] molecule which non-covalently links the polymeric molecule and the attachment compound in a supramolecular polymer. These polymers are useful as vehicles for delivery of a therapeutic compound for use in a method of treatment of the human or animal body, in particular for use in a method of delivering the therapeutic compound to a target site in an individual. The invention also provides methods for the preparation of the supramolecular polymers.

22 Claims, 13 Drawing Sheets

OTHER PUBLICATIONS

Bosman et al.; "Supramolecular polymers at work;" *Materials Today*; Apr. 2004; pp. 34-39; vol. 7; Elsevier Ltd.

Subesma et al.; "Reversible Polymers Formed from Self-Complementary Monomers Using Quadruple Hydrogen Bonding;" *Science*; 1997; pp. 1601-1604; vol. 278; American Association for the Advancement of Science; Washington D.C.

Archer et al.; "Coordination chemistry from monomers to copolymers;" *Coordination Chemistry Reviews*; 1993; pp. 49-68; vol. 128; Elsevier Sequoia.

Swiegers et al.; "New Self-Assembled Structural Motifs in Coordination Chemistry;" *Chem. Rev.*; 2000; pp. 3483-3537; vol. 100; American Chemical Society.

Lehn et al.; "Spontaneous assembly of double-stranded helicates from oligobipyridine ligands and copper(I) cations: Structure of an inorganic double helix;" *Proc. Natl. Acad. Sci.*; May 1987; pp. 2565-2569; vol. 84.

Schütte et al.; "Metallosupramolecular Thin Polyelectrolyte Films;" *Angew. Chem. Int. Ed.*; 1998; pp. 2891-2893; vol. 37, No. 20; Wiley-VCH Verlag GmbH & Co.

Lohmeijer et al.; "Supramolecular Engineering with Macromolecules: An Alternative Concept for Block Copolymers;" *Angew. Chem. Int. Edu.*; 2002; pp. 3825-3829; vol. 41, No. 20; Wiley-VCH Verlag GmbH & Co.

Chen et al; "Ruthenuim Bipyridine-Containing Polymers and Block Copolymers via Ring-Opening Metathesis Polymerization;" *Macromolecules*; 2004; pp. 5866-5872; vol. 37; American Chemical Society.

Zhou et al,; "Synthesis and Characterization of Bis(2,2':6'2"-terpyridince)ruthenium(II)-Connected Diblock Polymers via RAFT Polymerization;" *Macromolecules*; 2005; pp. 4114-4123; vol. 38; American Chemical Society.

Fustin et al.; "Metallo-Supramolecular Block Copolymers:" *Advanced Materials*; 2007; pp. 1665-1673; vol. 19; Wiley-VCH Verlag GmbH & Co.

Scherman et al.; "Olefin metathesis and quadruple hydrogen bonding: A powerful combination in multistep supramolecular synthesis;" *PNAS*; Aug. 8, 2006; pp. 11850-11855; vol. 103, No. 32; The National Academy of Sciences of the USA.

Yang et al.; "Supramolecular AB Diblock Copolymers;" *Angew. Chem. Int. Ed.*; 2004; pp. 6471-6474; vol. 43; Wiley-VCH Verlag GmbH & Co.

Higley et al.; "A Modular Approach toward Block Copolymers;" *Chem. Eur. J.*; 2005; pp. 2946-2953; vol. 11; Wiley-VCH Verlag GmbH & Co.

Yamauchi et al.; "Combinations of Microphase Separation and Terminal Multiple Hydrogen Bonding in Novel Macromolecules;" *J. Am. Chem. Soc.*; 2002; pp. 8599-8604; vol. 124; American Chemical Society.

Binder et al.; "Supramolecular Poly(ether ketone)-Polyisobutylene Pseudo-Block Copolymers;" *Journal of Polymer Science: Part A: Polymer Chemistry*; 2004; pp. 162-172; vol. 42; Wiley Periodicals, Inc.

Söntjens et al.; Stability and Lifetime of Quadruply Hydrogen Bonded 2-Ureido-4[1*H*]-pyrimidinone Dimers; *J. Am. Chem. Soc.*; 2002; pp. 7487-7493; vol. 122; American Chemical Society.

Shimizu; "Mini Review-Perspectives on main-chain hydrogen bonded supramolecular polymers;" *Polymer International*; 2007; pp. 444-452; vol. 56; Society of Chemical Industry.

Behrend et al.; "Justus Liebig's Annalen Der Chemie.;" 1905; pp. 1-37; vol. 339.

Freeman et al.; "Cucurbituril;" *J. Am. Chem, Soc.*; 1981; pp. 7367-7368; vol. 103; American Chemical Society.

Kim et al.; "New Cucurbituril Homologues: Syntheses, Isolation, Characterization, and X-ray Crystal Structures of Cucurbit[*n*]uril (n=5, 7, and 8);" *J. Am. Chem. Soc.*; 2000; pp. 540-541; vol. 122; American Chemical Society.

Lagona et al.; "The Cucurbit[*n*]uril Family;" *Angew. Chem. Int. Ed.*; 2005; pp. 4844-4870; vol. 44; Wiley-VCH Verlag GmbH & Co.

Kim et al.; "Selective Inclusion of a Hetero-Guest Pair in a Molecular Host: Formation of Stable Charge-Transfer Complexes in Cucurbit[8]uril;" *Angew. Chem. Int. Ed.*; 2001; pp. 1526-1529; vol. 40, No. 8; Wiley-VCH Verlag GmbH.

Sindelar et al.; "Supramolecular Assembly of 2,7-Dimethyldiazapyrenium and Cucurbit[8]uril: A New Fluorescent Host for Detection of Catechol and Dopamine;" *Chem. Eur. J.*; 2005; pp. 7054-7059; Vol, 11; Wiley-VCH Verlag GmbH & Co.

Bush et al.; "Charge-Mediated Recognition of N-Terminal Tryptophan in Aqueous Solution by a Synthetic Host;" *J. Am. Chem. Soc.*; 2005; pp. 14511-14517; vol. 127; American Chemical Society.

Jeon et al.; "Supramolecular Amphiphiles: Spontaneous Formation of Vesicles Triggered by Formation of a Charge-Transfer Complex in a Host;" *Angew. Chem. Int. Ed.*; 2002; pp. 4474-4476; vol. 41, No. 23; Wiley-VCH Verlag GmbH & Co.

Jeon et al.; "Molecular Loop Lock: A Redox-Driven Molecular Machine Based on a Host-Stablized Charge-Transfer Complex;" *Angew. Chem. Int. Ed.*; 2005; pp. 87-91; vol. 44; Wiley-VCH Verlag GmbH & Co.

Ko et al.; "Designed Self-Assembly of Molecular Necklaces Using Host-Stabilized Charge-Transfer Interactions;" *J. Am. Chem. Soc.*; 2004; pp. 1932-1933; vol. 126; American Chemical Society.

Kim et al.; "Growth of poly(pseudorotaxane) on gold using host-stabilized charge-transfer interaction;" *Chem. Commun.*; 2004; pp. 848-849; The Society of Chemistry.

Jeon et al.; "A [2]Pesudorotaxane-Based Molecular Machine: Reversible Formation of a Molecular Loop Driven by Electrochemical and Photochemical Stimuli;" *Angew. Chem, In, Ed.*; 2003; pp. 4097-4100; vol. 42; Wiley-VCH Verlag GmbH & Co.

Ko et al.; "Supramolecular assemblies built with host-stabilized charge-transfer interactions;" *Chem. Commun.*; 2007; pp. 1305-1315; The Royal Society of Chemistry.

Moon et al.; "Cucurbit[8]uril-Mediated Redox-Controlled Self-Assembly of Viologen-Containing Dendrimers;" *Angew. Chem. Int. Ed.*; 2004; pp. 5496-5494; vol. 43; Wiley-VCH Verlag GmbH & Co.

Wang et al.; "Electrochemical Switching and Size Selection in Cucurbit[8]uril-Mediated Dendrimer Self-Assembly;" *Angew. Chem. Int. Ed.*; 2006; pp. 7042-7046; vol. 45; Wiley-VCH Verlag GmbH & Co.

Floudas et al.; "Poly(ethylene oxide-*b*-isoprene) Diblock Copolymer Phase Diagram;" *Macromolecules*; 2001; pp. 2947-2957; vol. 34; American Chemical Society.

Hwang et al,; "Noncovalent Immobilization of Proteins on a Solid Surface by Cucurbit[7]uril-Ferrocenemethylammonium Pair, a Potential Replacement of Biotin-Avidin Pair;" *J. Am. Chem. Soc.*; 2007; pp. 4170-4171; vol. 129; American Chemical Society.

Sun et al.; "The photoinduced long-lived charge-separated state of Ru(bpy)$_3$-methylviologen with cucurbit[8]uril in aqueous solution;" *Chem. Commun*; 2006; pp. 4195-4197; The Royal Society of Chemistry.

Jon et al.; "A facile, stereoselective [2+2] photoreaction mediated by cucurbit[8]uril;" *Chem. Commun.*; 2001; pp. 1981-1939; The Royal Society of Chemistry.

Rauwald et al.; "Supramolecular Block Copolymers with Cucurbit[8]uril in Water;" *Angew. Chem. Int. Ed.*; 2008; pp. 3950-3953; vol. 47; Wiley-VCH Verlag GmbH & Co.

Broeren et al.; "Multivalency in the Gas Phase: The Study of Dendritic Aggregates by Mass Spectrometry;" *Angew. Chem. Int. Ed.*; 2004; pp, 3557-3562; vol. 43; Wiley-VCH Verlag GmbH & Co.

Osaka et al.; "Characterization of host-guest complexes of cucurbit[*n*]iuril (n=6,7) by electrospray ionization mass spectrometry;" *J. Mass Spectrom*; 2006; pp. 202-207; vol. 41; John Wiley & Sons, Ltd.

Brunsveld et al.; "Supramolecular Polymers;" *Chem. Rev.*; 2001; pp. 4071-4097; vol. 101; American Chemical Society,.

Knapp et al.; "A Novel Synthetic Strategy toward Soluble, Well-Defined Ruthenium(II) Coordination Polymers," *Macromolecules*; 1996; pp. 478-480; vol. 29; American Chemical Society.

Kim et al.; "Direct Synthesis of Polymer Nanocapsules with a Noncovalently Tailorable Surface.," *Angew. Chem. Int. Ed.*; 2007; pp. 3471-3474; Wiley-VCH Verlag GmbH & Co.

Ligthart et al.; "Supramolecular Polymer Engineering;" *Macromolecular Engineering, Precise Synthesis, Materials Properties, Applications*; 2007; pp. 351-399; Wiley-VCH Verlag GmbH & Co.

International Search Report mailed on Nov. 11, 2009 in corresponding International Application No. PCT/GB2008/004016.

Written Opinion of the International Searching Authority mailed on Nov. 11, 2009 in corresponding International Application No. PCT/GB2008/004016.

* cited by examiner (a) Main-chain supramolecular polymers (a) Side-chain supramolecular polymers

SUPRAMOLECULAR HANDCUFFS IN POLYMERIC ARCHITECTURE

This invention relates to the non-covalent linkage of molecules to produce supramolecular polymeric systems.

Supramolecular polymers have expanded the scope of polymer science allowing for the design and development of responsive and dynamic materials.[1-3] While traditional synthetic polymers are covalently-linked macromolecules, supramolecular polymer systems contain non-covalent binding sites either along the main-chain or as pendant side-chains. Specific control at these binding sites can often be modulated through an external handle thus leading to stimuli-responsive materials. A wide range of non-covalent interactions has been used successfully for the creation of supramolecular polymers including most prominently hydrogen bonding arrays[1, 4] and metal ligand interactions.[5-9] Furthermore, the formation of block copolymers via coordinate bonds that are stable even in aqueous media has been demonstrated recently.[10-13] In these specific instances, however, the metal-ligand interactions employed forfeit much of the dynamic nature of reversible binding that characterizes supramolecular materials. Moreover, the incorporation of metal centers in self-assembled polymers may jeopardize their use in biological environments and therefore an all-organic approach might be preferred.

In an effort to harness reversibility, supramolecular materials have been previously described which utilize multiple hydrogen bonding motifs in linear arrays for linking either small molecule or polymeric building blocks.[4, 14-18] While these systems display unique material properties in common organic solvents, where association constants are high, they have not successfully been replicated in aqueous environments. This is on account of the water molecules disrupting binding as they compete for the hydrogen bonding sites.[19, 20]

Cucurbit[8]uril simultaneously binds to two organic guest molecules with high association constants ($K_a \approx 10^{11} M^{-2}$) in an aqueous environment.[25-27] Earlier work by Kim et al. has demonstrated that a stable charge-transfer (CT) complex is formed inside the cavity of CB[8] between electron-deficient viologens and electron-rich aromatic units such as naphthalene derivatives.[25] CT complexes of CB[8] have been utilized for the formation of vesicles, a molecular loop lock or the self-assembly of a molecular necklace as well as a poly(pseudorotaxane) from small molecule guests.[28-33] Kaifer et al. have also employed this principle to connect asymmetric dendritic units.[34, 35]

The present inventors have discovered that cucurbit[8]uril (CB[8]) may be used to non-covalently join macromolecules, and particularly polymers, either with small molecule conjugates or with other macromolecules in aqueous media through the formation of a ternary host-guest complex. These complexes are strong and exhibit covalent-like properties, but remain in dynamic equilibria that can be controlled (addressed) by external stimuli such as electrochemical potential, pH, light, oxygen or temperature. Therefore, polymeric architectures produced in this way may be useful in a wide range of applications.

An aspect of the invention provides a method of producing a supramolecular polymer comprising;
providing a polymeric molecule linked to a first CB[8] guest molecule and an attachment compound linked to a second CB[8] guest molecule,
allowing the first and second CB[8] guest molecules to interact with a CB[8] molecule to form a ternary host-guest complex,
wherein said complex non-covalently links the polymeric molecule and the attachment compound in a supramolecular polymer.

In some embodiments, a method of producing a supramolecular polymer may comprise;
providing a polymeric molecule linked to a first CB[8] guest molecule and an attachment compound linked to a second CB[8] guest molecule,
(a) contacting the polymeric molecule with a CB[8] molecule such that the first CB[8] guest molecule and the CB[8] molecule interact to form a first complex, and contacting the first complex with the attachment compound such that the second CB[8] guest molecule interacts with the CB[8] molecule and the first CB[8] guest molecule to form a second complex; or
(b) contacting the attachment compound with a CB[8] molecule such that the second CB[8] guest molecule and the CB[8] molecule interact to form a first complex, and contacting the first complex, with the polymeric molecule such that the first CB[8] guest molecule interacts with the CB[8] molecule and the first CB[8] guest molecule and the second CB[8] guest molecule to form a second complex;
the second complex non-covalently linking the polymeric molecule and the attachment compound in a supramolecular polymer.

Another aspect of the invention provides a supramolecular polymer comprising a polymeric molecule linked to a first CB[8] guest molecule and an attachment compound linked to a second CB[8] guest molecule,
wherein the first and second CB[8] guest molecules form a ternary host-guest complex with a CB[8] molecule which non-covalently links the polymeric molecule and the attachment compound in a supramolecular polymer.

In one embodiment, the supramolecular polymer comprises a polymeric molecule linked to two or more first CB[8] guest molecules and an attachment compound linked to a second CB[8] guest molecule, wherein the first and second CB[8] guest molecules form ternary host-guest complexes with two or more CB[8] molecules which non-covalently link the polymeric molecule and the attachment compound in a supramolecular polymer.

In another embodiment, the supramolecular polymer comprises a polymeric molecule linked to a first CB[8] guest molecules and an attachment compound linked to two or more second CB[8] guest molecules, wherein the first and second CB[8] guest molecules form ternary host-guest complexes with two or more CB[8] molecules which non-covalently link the polymeric molecule and the attachment compound in a supramolecular polymer.

A suitable supramolecular polymer may be produced by a method described above. The supramolecular polymer is obtained or obtainable by the methods described herein.

The present inventors have also discovered that cucurbit[7]uril (CB[7]) and cucurbit[8]uril (CB[8]) may be used to non-covalently join polymers either with small molecule conjugates or with other polymers in aqueous media through the formation of a host-guest complex with ferrocene derivatives.

Another aspect of the invention provides a method of producing a supramolecular polymer comprising;
providing a polymeric molecule linked to one of a CB[8] molecule and a ferrocene CB[8] guest molecule, and an attachment compound linked to the other of a CB[8] molecule and a ferrocene CB[8] guest molecule, allowing the ferrocene CB[8] guest molecule to interact with the CB[8] molecule to form a host-guest complex, wherein said complex non-covalently links the polymeric molecule and the attachment compound in a supramolecular polymer.

Another aspect of the invention provides a supramolecular polymer comprising a polymeric molecule linked to one of a CB[8] molecule and a ferrocene CB[8] guest molecule, and an attachment compound linked to the other of a CB[8] molecule and a ferrocene CB[8] guest molecule, wherein the ferrocene CB[8] guest molecule and the CB[8] molecule form a host-guest complex which non-covalently links the polymeric molecule and the attachment compound in a supramolecular polymer.

A suitable supramolecular polymer may be produced by a method described above.

In some embodiments, the host-guest complex may be formed in aqueous solution, for example by admixing the components of the complex in an aqueous solution. The host-guest complex may form spontaneously in water or vigorous shaking and/or mixing may be required, for example when the CB[8] guest molecules are hydrophobic.

In other embodiments, the host-guest complex may be formed in aqueous solution in organic solvents using counter ions such as $PF_6^-$.

Cucurbit[8]uril (CB[8]; CAS 259886-51-6) is a barrel shaped container molecule which has eight repeat glycoluril units and an internal cavity size of 479Å$^3$ (see structure below). CB[8] is readily synthesised using standard techniques and is available commercially (e.g. Sigma-Aldrich, MO USA).

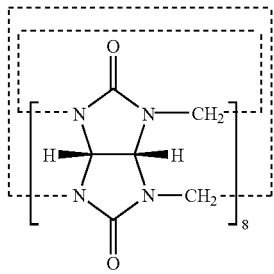

In other aspects of the invention, CB[8] variants are provided and find use in the methods described herein. A variant of CB[8] may be a structure having more than 8 repeat glycoluril units, for example CB[10] or less than 8 repeat glycoluril units, for example CB[7]. CB[7] forms very strong 1:1 complex with ferrocene derivatives ($K_a \approx 10^{12}$ M$^{-1}$) (Hwang, I. et al J. Am. Chem. Soc. 2007, 129, 4170-4171) and may be preferred for the production of supramolecular polymers which comprise ferrocene derivative as a guest molecule, as described above. CB[8] may also be used in such embodiments.

A variant of CB[8] may also include a structure having one or more repeat units that are structurally analogous to glycoluril. The repeat unit may include an ethylurea unit. Where all the units are ethylurea units, the variant is a hemicucurbituril. The variant may be a hemicucurbit[12]uril (shown below).[24]

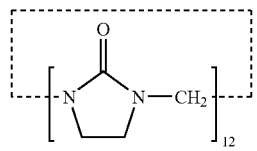

In other aspects of the invention, CB[8] derivatives are provided and find use in the methods described herein. A derivative of CB[8] is a structure having one or more substituted glycoluril units. A substituted CB[8] compound may be represented by the structure below:

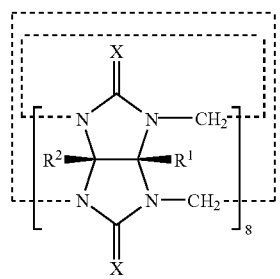

Wherein X is O, S or NR$^3$, and —R$^1$ and —R$^2$ are each independently selected from —H and the following optionally substituted groups: —R$^3$, —OH, —OR$^3$, —COOH, —COOR$^3$, —NH$_2$, —NHR$^3$ and —N(R$^3$)$_2$ where —R$^3$ is independently selected from C$_{1-20}$alkyl, C$_{6-20}$-carboaryl, and C$_{5-20}$heteroaryl, or where —R$^1$ and/or —R$^2$ is —N(R$^3$)$_2$, both —R$^3$ together form a C$_{5-7}$ heterocyclic ring; or together —R$^1$ and —R$^2$ are C$_{4-6}$alkylene forming a C$_{6-8}$-carbocyclic ring together with the uracil frame. It is preferred that —R$^1$ and —R$^2$ are not both —H.

Preferably, X is O.

Preferably —R$^3$ is C$_{1-20}$alkyl, most preferably C$_{1-6}$alkyl. The C$_{1-20}$alkyl group may be linear and/or saturated. Each group —R$^3$ may be independently unsubstituted or substituted. Preferred substituents are selected from: —R$^4$, —OH, —OR$^4$, —SH, —SR$^4$, —COOH, —COOR$^4$, —NH$_2$, —NHR$^4$ and —N(R$^4$)$_2$, wherein —R$^4$ is selected from C$_{1-20}$alkyl, C$_{6-20}$-carboaryl, and C$_{5-20}$heteroaryl. The substituents may be independently selected from —COOH and —COOR$^4$.

In some embodiments, —R$^4$ is not the same as —R$^3$. In some embodiments, —R$^4$ is preferably unsubstituted.

Where —R$^1$ and/or —R$^2$ is —OR$^3$, —NHR$^3$ or —N(R$^3$)$_2$, then —R$^3$ is preferably C$_{1-6}$alkyl. In some embodiments, —R$^3$ is substituted with a substituent —OR$^4$, —NHR$^4$ or —N(R$^4$)$_2$. Each —R$^4$ is C$_{1-6}$alkyl and is itself preferably substituted. In one embodiment, —R$^1$ and/or —R$^2$ may be a polyalkylene glycol substituent, for example a polyethylene glycol substituent, or a spermine substituent.

In some embodiments, —R$^1$ and/or —R$^2$ may be a linker to a second polymeric molecule. The second polymeric molecule may be a molecule as defined for the polymeric molecules described herein. It is preferred that the second polymeric molecule and the polymeric molecule are not covalently linked. It is preferred that the polymeric molecule and the second polymeric molecule are not the same.

The substituents —R$^1$ and —R$^2$ may be the same or different. Preferably they are the same. In one embodiment, —R$^1$ and/or —R$^2$ may be unsubstituted.

In some embodiments, variants of derivatives of CB[8] are provided and find use in the methods described herein.

Where reference is made to CB[8] herein, such reference may also include a reference to a variant, derivative, or variant of a derivative of CB[8] as described above.

In other embodiments, the CB[8] variant or derivative is a compound as described in WO 2007/046575, which is incorporated by reference herein.

The attachment compound is incorporated into the supramolecular polymer via non-covalent linkage to the polymeric molecule. Any suitable attachment compound may be employed.

In some embodiments, the attachment compound may be a small organic molecule. For example, the attachment compound may be a detection label, such as a radionuclide or fluorophore, or a biologically active or therapeutic compound which exhibits a therapeutic or prophylactic effect in vivo, or a biological effect in vitro. Suitable therapeutic compounds may be capable of triggering a biocidal event, and may include radionuclides, photosensitisers, drugs, or toxins. The therapeutic compound may be hydrophobic or insoluble. Examples of water-insoluble therapeutic compounds include doxorubicin, and paclitaxel.

In other embodiments, the attachment compound may be a polymeric molecule. In such embodiments, the polymeric molecule attached to the first CB[8] guest molecule is conveniently referred to as the 'first polymeric molecule' and the polymeric molecule attached to the second CB[8] guest molecule is conveniently referred to as the 'second polymeric molecule'. The first polymeric molecule may be the same as the second polymeric molecule or the two polymeric molecules may be different. The use of two different polymeric molecules allows the production of supramolecular block co-polymers. The first and second polymeric molecules may have different properties. For example, the first polymeric molecule may be a hydrophilic polymer and the second polymeric molecule may be a hydrophobic polymer or vice versa to produce an amphiphilic block-co-polymer.

Polymeric molecules comprise a plurality of repeating structural units (monomers) which are connected by covalent bonds. Polymeric molecules may comprise a single type of monomer (homopolymers), or more than one type of monomer (co-polymers). Polymeric molecules may be straight or branched. Where the polymeric molecule is a co-polymer, it may be a random, alternating, periodic, statistical, or block polymer, or a mixture thereof. The co-polymer may also be a graft polymer.

In one embodiment, the polymeric molecule has 2, 3, 4 or 5 repeat units. For convenience, such a polymer may be referred to as an oligomer.

In other embodiments, the polymeric molecule has 4 or more, 8 or more, 15 or more, 100 or more, 1,000 or more monomer units. The number of units may be an average number of units.

Preferably, the polymeric molecule has a molecular weight ($M_W$) of greater than 500, greater than 1000, greater than 2000, greater than 3000 or greater than 4000. The molecular weight may be the weight average molecular weight or the number average molecule weight.

The number average and weight average molecular weights of a polymer can be determined by conventional techniques.

In preferred embodiments, the polymer is a synthetic polydisperse polymer. A polydisperse polymer comprises polymeric molecules having a range of molecular masses. The polydispersity index (PDI) (weight average molecular weight divided by the number average molecular weight) of a polydisperse polymer is greater than 1, and may be in the range 5 to 20. The polydispersity of a polymeric molecule may be determined by conventional techniques such as gel permeation or size exclusion chromatography.

Many polymeric molecules are known in the art and may be used to produce supramolecular polymers as described herein. The choice of polymeric molecule will depend on the particular application of the supramolecular polymer. Suitable polymeric molecules include natural polymers, such as protein, nucleic acid, glycosaminoglycan or polysaccharide, or synthetic polymers, such as polyethylene glycol (PEG) and cis-1,4-polyisoprene (PI). Other suitable polymeric molecules include rigid rod polymers and semi-conducting polymers, such as poly(pyrolle) and poly(thiophene), and those polymers based on poly(p-phenylene) (PPP). The polymeric molecule may comprise two or more natural and synthetic polymers.

Suitable polymeric molecules include hydrophilic polymers. A hydrophilic polymer is amenable to wetting and forms hydrogen bonds in a polar solvent, such as water. Hydrophilic polymers are therefore soluble in aqueous solutions to form a continuous phase. Examples of hydrophilic polymers include polyethylene glycol (PEG), poly-ethylene oxide (PEO), polyvinyl pyrrolidone (PVP), hydroxypropyl methylcellulose (HPMC) polypropylene, polyvinyl alcohol, polyacrylmorpholine Polyacrylic acid, poly(styrene sulfonate), poloxamers in general (PEO-PPO blocks), polyglycerol, polydimethylacrylamide (PDMA) or a derivatives or copolymers thereof. In some embodiments, the first polymeric molecule is a hydrophilic polymer, such as PEG.

Other polymeric molecules suitable for use include poly (N-isopropylacrylamide) (PNIPAM) or double-hydrophilic diblock copolypeptides (BCPs) such as poly(glutamic acid)-block-poly(N-isopropylacrylamide) ($PLG_nPN_m$) or derivatives thereof.

In some embodiments, the polymeric molecule is a polyakylene gycol, most preferably PEG. The number of repeat alkylene glycol units in the polyakylene glycol may be low, for example 2, 3, 4 or 5 repeat units. Preferably, the number of repeat alkylene glycol units is 3 or more.

In other embodiments, the number of repeat alkylene glycol units in the polyakylene glycol is high, for example the average molecular weight of the polyakylene glycol is greater than 1,000 or greater than 1,500.

Suitable polymeric molecules also include hydrophobic polymers. A hydrophobic polymer is not amenable to wetting and is incapable of forming hydrogen bonds in a polar solvent, such as water. Hydrophobic polymers are therefore immiscible in aqueous solvents and form a separate phase. Examples of hydrophobic polymers include polyolefins, such as poylethylene, poly(isobutene), poly(isoprene), cis-1,4-polyisoprene, poly(4-methyl-1-pentene), polypropylene, polypropylene oxide, polythiopene, ethylene-propylene copolymers, and ethylene-propylene-hexadiene copolymers; ethylene-vinyl acetate copolymers; styrene polymers, such as poly(styrene) and poly(2-methylstyrene), polyacrylonitrile, polyvinylchloride, polyacrylate, poly(methyl acrylate) and celluloses such as amylose, amylopectin, cellulose acetate butyrate, ethyl cellulose, hemicellulose, and nitrocellulose.

In some embodiments, the polymeric molecule may comprise monomer units that that are hydrophobic and monomer units that are hydrophilic. These monomer units may be arranged alternatively, randomly or in blocks. Alternatively, the main chain may be one polymer type (for example poly (styrene)), and the branches may be of another polymer type (for example, PEG).

In some embodiments, the first polymeric molecule and/or second polymeric molecule may be proteins or polypeptides, for example, binding proteins such as bradykinin, and antibodies or antibody fragments.

For example, the first polymeric molecule may be a specific binding member such as an antibody. A supramolecular polymer as described herein may comprise an antibody molecule linked to a first CB[8] guest molecule and an attachment compound linked to a second CB[8] guest molecule,
  wherein the first and second CB[8] guest molecules form a ternary host-guest complex with a CB[8] molecule which non-covalently links the antibody molecule and the attachment compound in a supramolecular polymer.

In some embodiments, a first and/or second polymeric compound which is a protein or polypeptide may be linked to the tripeptide WGG, which is a known CB[8] guest molecule.

The attachment molecule non-covalently linked to a polypeptide, such as an antibody, as described herein, may be a small organic molecule, in particular a label or therapeutic compound as described above.

In other embodiments, the second polymeric molecule may be a biologically active or therapeutic polypeptide. Suitable therapeutic polypeptides include antibodies, cytokines, transcription factors, hormones, chemokines, pro-coagulant factors, or enzymes.

Typically, a polypeptide for use as described herein comprises 5 or more, 10 or more, 15 or more, 20 or more or 30 or more amino acid residues.

The polymeric molecule and the attachment compound are preferably linked to the first and second CB[8] guest molecules respectively by covalent bonds. The covalent bond may be a carbon-carbon bond, a carbon-nitrogen bond, a carbon-oxygen bond. The bond may be part of a linking group such as an ester or an amide.

Where the polymeric molecule is a polypeptide, such as an antibody, the polymeric molecule and the guest molecule may be linked through a thiother bond. Such a bond may be formed from the reaction between e.g. a cysteine thiol of the polypeptide and a maleimide group connected to the guest compound.

In other embodiments, the polymeric molecule and the attachment compound are linked to the first and second CB[8] guest molecules by orthogonal non-covalent interactions, such as a phosphorous-boron bond.

The polymeric molecule and the attachment compound may be linked directly to the first and second CB[8] guest molecules or indirectly, for example via a linker. Suitable linkers are well-known in the art.

In some embodiments, the polymeric compound and the attachment compound may be connected by an additional covalent or non-covalent linkage, in addition to the non-covalent linkage through the guest-host ternary complex described herein. In other embodiments, the polymeric compound and the attachment compound are not linked other than non-covalently through the guest-host ternary complex, as described herein.

The first and second CB[8] guest molecules may be linked to the polymeric molecule and the attachment compound using routine chemical linkage techniques. For example, first and second CB[8] guest molecules may be linked to the polymeric molecule and the attachment compound by: alkylation of a polymer bearing an appropriate leaving group; esterification reactions; amidation reactions; ether forming reactions; olefin cross metathesis; or small guest molecule initiated reactions in which the polymer chain is grown off an initiating guest molecule.

A CB[8] guest molecule may be derived from, or contain, a structure from the table below:

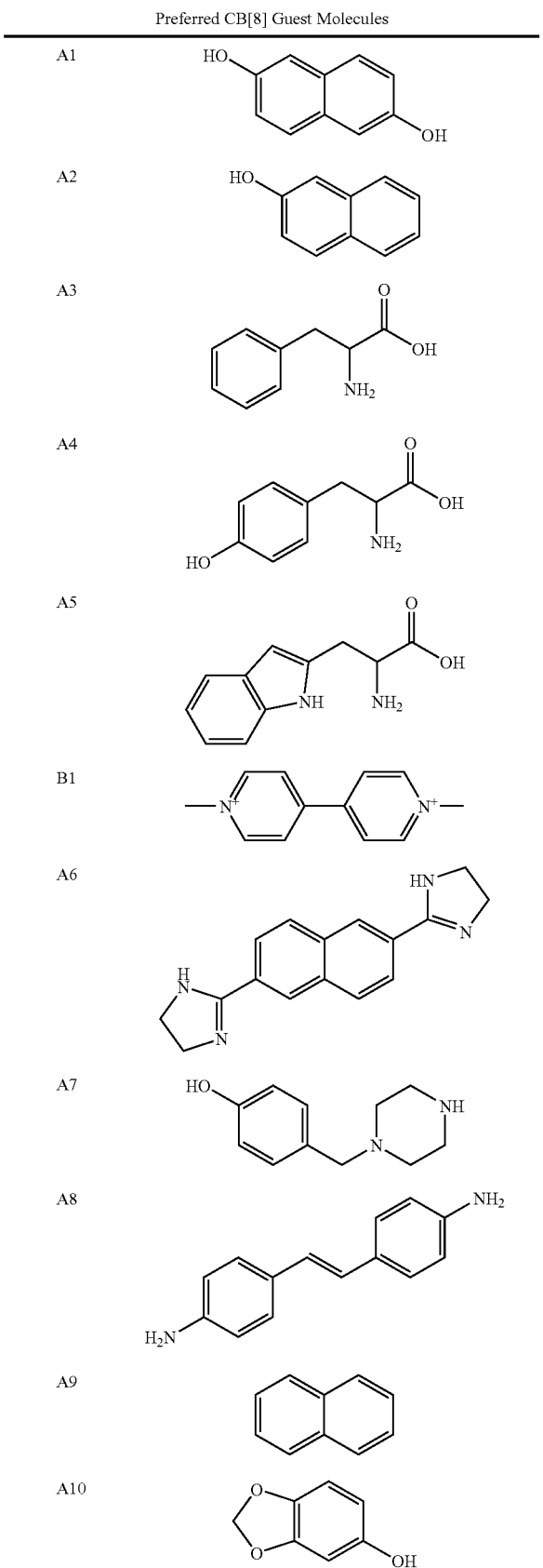

| Preferred CB[8] Guest Molecules |
|---|

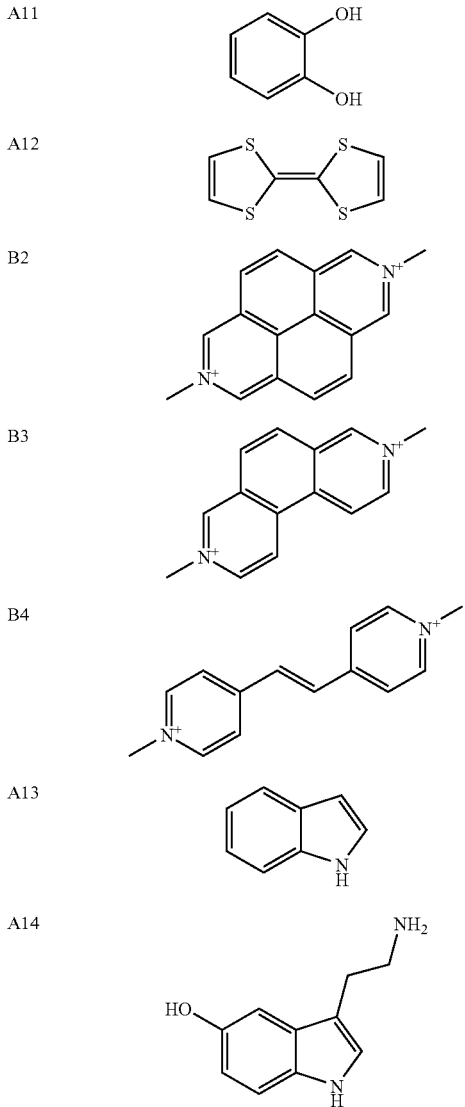

| A11 | |
| A12 | |
| B2 | |
| B3 | |
| B4 | |
| A13 | |
| A14 | | where the structure may be a salt, including protonated forms, where appropriate.

In one embodiment, the guest molecule is, or is derived from, or contains, structure A1, A2, or A13 in the table above.

Other suitable guest molecules include, or are derived from, or contain, the following compounds:

| Preferred CB[8] Guest Molecules |
|---|

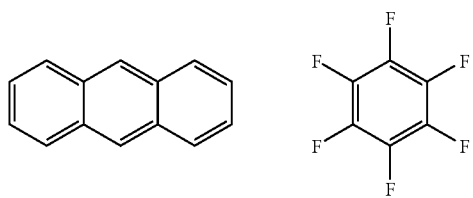

The first and second CB[8] guest molecules form a pair which may interact within the cavity of CB[8] to form a stable ternary host-guest complex. Any guest pair that fits within the cavity of CB[8] may be employed.

In some embodiments, the guest molecules may form a charge transfer pair comprising an electron-rich and an electron-deficient compound. One of the first and second guest molecules acts as an electron acceptor and the other as an electron donor in the CT pair. For example, the first CB[8] guest molecule may be an electron deficient molecule which acts an electron acceptor and the second CB[8] guest molecule may be an electron rich molecule which acts as an electron donor or vice versa.

Suitable electron acceptors include 4,4'-bipyridinium derivatives, for example N,N'-dimethyldipyridyliumylethylene, and other related acceptors, such as those based on diazapyrenes and diazaphenanthrenes. Viologen compounds including alkyl viologens are particularly suitable for use in the present invention. Examples of alkyl viologen compounds include N,N'-dimethyl-4,4'-bipyridinium salts (also known as Paraquat).

Suitable electron donors include electron-rich aromatic molecules, for example 1,2-dihydroxybenzene, 1,3-dihydroxybenzene, 1,4-dihydroxybenzene, tetrathiafulvalene, naphthalenes such as 2,6-dihydroxynaphthalene and 2-naphthol, indoles and sesamol (3,4-methylenedioxyphenol). Polycyclic aromatic compounds in general may find use as suitable electron donors in the present invention. Examples of such compounds include anthracene and naphthacene.

Amino acids, such as tryptophan, tyrosine and phenylalanine may be suitable for use as electron donors. Peptide sequences comprising these amino acids at their terminus may be used. For example, a donor comprising an amino acid sequence N-WGG-C, N-GGW-C or N-GWG-C may be used.

In some embodiments, the guest molecules are a pair of compounds, where one of the pair is an A compound as set out in the table above (e.g. A1, A2, A3 etc.), and the other of the pair is a B compound as set out in the table above (e.g. B1, B2, B3 etc.).

Other suitable guest molecules include peptides such as WGG (Bush, M. E. et al *J. Am. Chem. Soc.* 2005, 127, 14511-14517).

An electron-rich CB[8] guest molecule may be paired up with any electron-deficient CB[8] guest molecule. Examples of suitable pairs of CB[8] guest molecules for use as described herein may include:
 viologen and naphthol;
 viologen and dihydroxybenzene;
 viologen and tetrathiafulvalene;
 viologen and indole;
 N,N'-dimethyldipyridyliumylethylene and naphthol;
 N,N'-dimethyldipyridyliumylethylene and dihydroxybenzene;
 N,N'-dimethyldipyridyliumylethylene and tetrathiafulvalene;
 N,N'-dimethyldipyridyliumylethylene and indole;
 2,7-dimethyldiazapyrenium and naphthol;
 2,7-dimethyldiazapyrenium and dihydroxybenzene;
 2,7-dimethyldiazapyrenium and tetrathiafulvalene; and
 2,7-dimethyldiazapyrenium and indole.

In particular, suitable pairs of CB[8] guest molecules for use as described herein may include 2-naphthol and methyl viologen, 2,6-dihydroxynaphthalene and methyl viologen and tetrathiafulvalene and methyl viologen.

In preferred embodiments, the attachment compound and/or the polymeric molecule are releasable from the supramolecular polymer, together with their respective guest molecules, preferably reversibly releasable.

In other embodiments, either the polymeric molecule or the attachment compound is connected to a modifiable surface. Examples include the surface of a carbon nanotube, a carbon nanowire or a glass, which may be in the form of a bead or a wire. Techniques for connecting molecules to these surfaces are well known in the art.

The attachment compound and/or the polymeric molecule may be released from the supramolecular polymer by the reduction or oxidation of a guest molecule within the supramolecular complex. The reduction or oxidation may be achieved by the application of an external stimulus, such as an electrochemical potential or a reducing agent, such as sodium dithionite, or an oxidising agent, such as oxygen. A guest molecule may be redox active. In one oxidation state the guest molecule may be capable of forming a charge transfer pair in the CB[8] host. In another oxidation state, the guest molecule may prefer a homo (or dimer) pairing in the CB[8] host. For example, viologen ($V^{2+}$) is capable of forming a charge transfer pair with a second, hetero guest molecule in CB[8]. Reduction of viologen from $V^{2+}$ to $V^+$ promotes the formation of a viologen dimer pair in CB[8], resulting in the exclusion of the second guest molecule from CB[8]. Such transformations may also be light-induced.[38, 39]

The attachment compound and/or the polymeric molecule may be released from the supramolecular polymer by changes in pH. In such methods, it is preferred that the guest molecule comprises a group that is pH sensitive, such as an amine or carboxylic acid. The protonation or deprotonation of a group in or around the binding region of the guest molecule may lead to the dissociation of the guest molecule from the charge-transfer complex, thereby resulting in the release of the guest molecule from the CB[8] host. The CB[8] cavity is an electron-rich environment, and is believed to repel guest having negatively-charged groups, such as carboxylates ($-COO^-$).

The attachment compound and/or the polymeric molecule may also be released from the supramolecular polymer through the affinity of an attachment compound for a target site in the vicinity of the polymer. Strong affinity for a target site drives the competitive binding equilibrium of the ternary complex towards dissociation, thereby releasing the attachment compound.

The attachment compound and/or the polymeric molecule may also be released from the supramolecular polymer through a competitive host-guest interaction. A competitor compound having a third CB[8] guest molecule may competitively displace one or both of the attachment compound and/or the polymeric molecule. The third CB[8] guest molecule may be selected from any of the guest molecules described above.

The attachment compound and/or the polymeric molecule may be released using a combination of any of the external stimuli described above.

In other embodiments, the attachment compound and/or the polymeric molecule may be released from the supramolecular assembly by separation of the attachment compound and/or the polymeric molecule from the respective guest molecule, the guest molecule/s remaining associated with the CB[8] molecule. The link between the attachment compound and/or the polymeric molecule and the guest molecule/s may be a cleavable link. Such a link may be cleaved by light, heat, an enzyme, a cleaving agent, such as a reducing agent, a nucleophile, or an acid or a base.

The nature of the external stimulus which releases the attachment compound and/or the polymeric molecule from the supramolecular polymer is dictated by the first and second CB[8] guest molecules employed. For example, when the CB[8] guest molecules are 2,6-dihydroxynaphthalene and methyl viologen, 2,6-dihydroxynaphthalene (and polymers or attachment compounds linked to it) may be released from the polymer by reduction, for example using a reducing agent, and re-incorporated into the polymer by oxidation, for example electrochemical oxidation. Similarly, when the CB[8] guest molecules are tetrathiafulvalene and methyl viologen, tetrathiafulvalene may be released and reincorporated by reduction and oxidation, respectively. In principle, all viologen-containing guest pairs may be released and reincorporated by reduction and oxidation. Likewise, in principle, all redox-active guest molecules within a guest pair may be released and reincorporated by reduction and oxidation.

The reversible release of a binding member in response to an external stimulus allows the supramolecular polymers described herein to be used in a molecular device.

Supramolecular polymers for use in molecular devices may comprise first and, optionally, second polymeric molecules which are hydrophobic polymers, such as polystyrenes, polyolefins and polythiophenes.

Other aspects of the invention relate to the use of supramolecular polymers as described herein to increase the solubility of compounds in aqueous solutions. This may be useful, for example, in solubilising therapeutic compounds in pharmaceutical compositions. The methods describe herein may also be useful for increasing the storage time of a therapeutic compound in aqueous solution by increasing the solubility of that compound.

For example, the attachment compound in a supramolecular polymer as described above may be a compound which has low solubility in aqueous solutions and the polymeric molecule in the supramolecular polymer may be a hydrophilic polymer. The non-covalent attachment of the low solubility compound to the hydrophilic polymer in the supramolecular polymer may increase its solubility in aqueous solution relative to the unattached compound.

A low solubility compound is a compound which either displays low solubility or is insoluble or substantially insoluble in aqueous solutions. Solubility is typically determined at neutral pH and ambient temperature and pressure. Methods for determining the solubility of a compound are well-known in the art (Remington: the Science and Practice of Pharmacy, I, 194-195 (Gennaro, ed., 1995)). For example, a compound may have low solubility if it requires at least 20 parts solvent to dissolve one part solute and may be water-insoluble if it requires at least 30 parts solvent to dissolve one part solute.

In some embodiments, the low solubility compound may be a therapeutic compound. The methods described herein may be useful in increasing the solubility of such a therapeutic compound. For example, a method of increasing the solubility of a therapeutic compound in aqueous solution may comprise;

providing a hydrophilic polymer linked to a first CB[8] guest molecule and a therapeutic compound linked to a second CB[8] guest molecule, allowing the first and second CB[8] guest molecules to interact with a CB[8] molecule to form a complex said complex non-covalently linking the hydrophilic polymer to the therapeutic compound to form a supramolecular polymer which has increased solubility in aqueous solution relative to the therapeutic compound.

As described above, the formation and dissociation of supramolecular polymers may be controlled by the application of stimuli. Methods described herein may therefore be useful in delivering a therapeutic compound to a target site in an individual. A method of delivering a therapeutic compound to a target site may comprise;

administering a supramolecular polymer comprising a hydrophilic polymer linked to a first CB[8] guest molecule and the therapeutic compound linked to a second CB[8] guest molecule, wherein the first and second CB[8] guest molecules are complexed with a CB[8] molecule to form the supramolecular polymer comprising the hydrophilic polymer and the therapeutic compound, allowing the supramolecular polymer to reach the target site and stimulating release of the therapeutic compound from the supramolecular polymer.

A target site is a site within the body of an individual at which imaging, labelling or therapy, including prophylaxis, may be required. A target site may, for example, include a site of tissue injury or damage or a tumour.

Any therapeutic compound which displays sub-optimal solubility, in particular low solubility, in aqueous solution may be used in the methods described herein. Suitable compounds include paclitaxel and doxorubicin Suitable hydrophilic polymers include poloxamers (PEO/PPO) and PEG block copolymers. Also the length of the polymer chain (avg. molecular weight 1000, 2000, 5000, 10000) may be optimized for this application. Preferably the guest molecule displays little or no toxicity. Examples of low toxicity guest molecules include indole, sesamol and/or amino acid based guest molecules, such as tryptophan and phenylalanine.

The supramolecular polymer comprising the therapeutic compound may be administered by any convenient means and in any convenient dosage as described below.

Another aspect of the invention provides a supramolecular polymer comprising a hydrophilic polymer linked to a first CB[8] guest molecule and a therapeutic compound linked to a second CB[8] guest molecule, wherein the first and second CB[8] guest molecules are complexed with a CB[8] molecule to form the supramolecular polymer comprising the hydrophilic polymer and the therapeutic compound, for use in a method of treatment of the human or animal body, in particular, for use in a method of delivering the therapeutic compound to a target site in an individual as described herein.

In some embodiments, the release of the therapeutic compound at the target site may be stimulated by applying a suitable external stimulus, such as electrochemical potential, pH, light, or oxygen. Temperature changes may also be used to release the therapeutic compound at the therapeutic site. The nature of the stimulus which is applied will depend on the CB[8] guest molecules which are employed. In other embodiments, the vicinity of the target site may stimulate release of the therapeutic compound. For example, the binding affinity of an attachment compound for the target site may drive the dissociation of the supramolecular polymer in the vicinity of the target site to release the attachment compound.

The methods described herein may also find use in microfluidic devices, where a low solubility compound, such as a reagent or a product, may be solubilised at one area of the device and then transported to another area of the device, where the compound may be selectively released.

Supramolecular polymers as described herein may comprise one type of polymeric molecule i.e. they may be homopolymers; or they may comprise two or more different polymeric molecules i.e. they may be block co-polymers.

A block co-polymer may comprise two or more units of each polymeric molecule. The block co-polymer may comprise one or more non-covalent guest-host complex linkages as described herein.

In other embodiments, a supramolecular polymer may comprise polymeric molecules non-covalently linked by guest-host ternary complexes as described herein to a linker compound. The linker compound may itself be non-covalently linked to another polymeric molecule by a guest-host ternary complex. The supramolecular polymer may comprise alternating sequences of polymeric molecules and linker compounds, or block sequences of each.

The linker compound may be an attachment compound as described previously, having two or more guest molecules, as described herein.

Other aspects of the invention relate to the production and use of such block co-polymers.

A block co-polymer may comprise:
a first polymeric molecule unit having CB[8] guest molecules at its termini; and,
(a) two units of a second polymeric molecule each having a CB[8] guest molecule at a terminal, or
(b) two units of a linker molecule each having a CB[8] guest molecule;
the units of the first and second polymeric molecule, or the units of the first polymeric molecule and the linker molecule, being non-covalently linked by ternary guest-host complexes comprising a CB[8] guest molecule on each unit and a CB[8] molecule.

Alternatively, a block co-polymer may comprise:
two units of a first polymeric molecule each having a CB[8] guest molecule at a terminal; and,
(a) a second polymeric molecule unit having CB[8] guest molecules at its termini, or
(b) a linker molecule unit having CB[8] guest molecules at its termini;
the units of the first and second polymeric molecule, or the units of the first polymeric molecule and the linker molecule, being non-covalently linked by ternary guest-host complexes comprising a CB[8] guest molecule on each unit and a CB[8] molecule.

A block co-polymer may comprise:
one or more of units a first polymeric molecules having CB[8] guest molecules at its termini; and,
(a) one or more units of a second polymeric molecule having CB[8] guest molecules at its termini, or
(b) one or more units of a linker molecule having two or more CB[8] guest molecules;
the units of the first and second polymeric molecule, or the units of the first polymeric molecule and the linker molecule, being non-covalently linked by ternary guest-host complexes comprising a CB[8] guest molecule on each unit and a CB[8] molecule.

Preferably, a block co-polymer may comprise:
one or more units of a first polymeric molecules having CB[8] guest molecules at its termini; and,
one or more units of a second polymeric molecule having CB[8] guest molecules at its termini,
the units of the first and second polymeric molecule being non-covalently linked by ternary guest-host complexes comprising a CB[8] guest molecule from a terminus of each unit and a CB[8] molecule.

Where a polymeric molecule or a linker molecule has two or more CB[8] guest molecules, the CB[8] guest molecules may be the same or they may be different. In a preferred embodiment, the CB[8] guest molecules are the same.

A terminus or termini as described herein may refer to the terminal region/s of a polymeric molecule. The terminal region may be on a main branch, a side branch or on a graft. The terminal region may be the terminal monomer unit, or one of at most the 3 monomer units contiguous with that terminal monomer unit. It is preferred that the terminus or termini is the terminal monomer unit.

In some embodiments, the first polymeric molecule or the second polymeric molecule, where present, is provided with three of more CB[8] guest molecules, which may be located at the termini of the main chain and the branches. Where the polymer is a star-type polymer, the guest molecules may be located at the termini of the arms of the star.

The guest molecules of the linker molecule may be located at any position in the linker structure. Preferably, the guest molecules are located at the termini of the linker molecule.

In some embodiments, the linker molecule, where present, comprises three or more CB[8] guest molecules. These may be located at any position on the linker molecule. Preferably, each guest molecule is located at a terminal, where appropriate.

A schematic of a star-type supramolecular polymer is shown in FIG. 12, in which a central linker having two or more CB[8] guest molecules is connected to a plurality of polymers each having a CB[8] guest molecule at a terminal. The CB[8] guest molecules interact with a cucurbit[8]uril (CB[8]) molecule to form a ternary host-guest complex linking the polymers to the central linker.

Where a polymeric molecule and/or a linker molecule has three or more CB[8] guest molecules, such compounds may be used to prepare branched supramolecular polymers or supramolecular polymers having a dendritic-type structure.

A block co-polymer may be produced by a method comprising;
  providing a population of first polymeric molecules having CB[8] guest molecules at their termini and (a) a population of second polymeric molecules having a CB[8] guest molecules at a terminal; 0r (b) a population of linker molecules each having a CB[8] guest molecule,
  contacting the populations of (a) first and second polymeric molecules; or (b) first polymeric molecules and linker molecules, with a population of CB[8] molecules, such that CB[8] guest molecules interact with CB[8] molecules to form ternary guest-host complexes,
  thereby producing a block co-polymer comprising (a) a plurality of first and second polymeric molecules non-covalently linked together by said complexes; or (b) a plurality of first polymeric molecules and linker molecules non-covalently linked together by said complexes.

A block co-polymer may be produced by a method comprising;
  providing a population of first polymeric molecules each having a CB[8] guest molecule at a terminal and (a) a population of second polymeric molecules each having CB[8] guest molecules at their termini; or (b) a population of linker molecules each having CB[8] guest molecules at their termini,
  contacting the populations of (a) first and second polymeric molecules; or (b) first polymeric molecules and linker molecules, with a population of CB[8] molecules, such that CB[8] guest molecules interact with CB[8] molecules to form ternary guest-host complexes,
  thereby producing a block co-polymer comprising (a) a plurality of first and second polymeric molecules non-covalently linked together by said complexes; or (b) a plurality of first polymeric molecules and linker molecules non-covalently linked together by said complexes.

A block co-polymer may be produced by a method comprising;
  providing a population of first polymeric molecules having CB[8] guest molecules at their termini and a population of second polymeric molecules having CB[8] guest molecules at their termini,
  contacting the populations of first and second polymeric molecules with a population of CB[8] molecules, such that CB[8] guest molecules interact with CB[8] molecules to form ternary guest-host complexes,
  thereby producing a block co-polymer comprising a plurality of first and second polymeric molecules non-covalently linked together by said complexes.

Preferred polymeric molecules for use in a co-polymer as described herein include PEGs and polyglycerols. Other suitable polymeric molecules are described above.

The polymeric molecules may be arranged in the co-polymer in any desired arrangement. Suitable arrangements of polymeric molecules include hydrophobic polymer-hydrophilic polymer, donor polymer-acceptor polymer, coil polymer-rod polymer or crystalline polymer-non-crystalline polymer.

Block co-polymers in any desired arrangement may be produced by various permutations of polymeric molecules and guest molecules. For example, the first polymeric molecules may have first CB[8] guest molecules at their termini and the second polymeric molecules may have second CB[8] guest molecules at their termini. The units of the first and second polymeric molecules are non-covalently linked by ternary guest-host complexes comprising a first and a second CB[8] guest molecule and a CB[8] molecule.

A schematic of a main chain supramolecular polymer is shown in FIG. 11(a), in which a plurality of first and second polymers, each having CB[8] guest molecules at their termini, and the CB[8] guest molecules interact with a cucurbit[8]uril (CB[8]) molecule to form a ternary host-guest complex linking the polymers.

The CB[8] guest molecules may be reversibly releasable from the ternary guest-host complexes linking the units polymeric molecules in response to an external stimulus as described above. The properties of the co-polymer may thus be controlled in situ.

A multiblock co-polymer may, for example, be created using two different polymeric molecules, or a polymeric molecule and a linker. For example, a first polymeric molecule may have a first CB[8] guest molecule at a first terminal, and a second polymeric molecule may have second CB[8] guest molecules at both its termini. Mixing the first and second polymeric molecules in solution will create a multiblock co-polymer (e.g. A-guest1+guest2-B-guest2+guest1-A+CB[8]→ABA type block). Where a linker is used in place of a polymeric molecule, it may replace either the first or second polymeric molecule.

As described above, co-polymers may comprise more than two types of polymeric molecule. A multiblock co-polymer may, for example, be created using more than two different polymeric molecules. For example, a first polymeric molecule may have a first CB[8] guest molecule at a first terminal, a second polymeric molecule may have second CB[8] guest molecules at both its termini, a third polymeric molecule may have first CB[8] guest molecules at both its termini and a fourth polymeric molecule may have second CB[8] guest molecules at a first terminal. Mixing the first, second, third and fourth polymeric molecules in aqueous solution will create a multiblock co-polymer (e.g. A-guest1+guest2-B-guest2+guest1-C-guest1+guest2-D+CB[8]→ABCD type block). The multiblock co-polymer comprising all four polymeric molecules may then be isolated from other polymer species in the solution using standard techniques.

Covalent interactions may be used in combination with the CB[8] motif to produce multiblock copolymers. For example, covalent diblock copolymers may be non-covalently linked to CB[8] as described herein to produce non-alternating multiblock co-polymers. (e.g. AB-guest1+CB[8]+guest2-CD→AB-CD type block).

Orthogonal non-covalent interactions may also be used in combination with the CB[8] motif to produce complex multiblock copolymers.

Inclusion of appropriate CB[8] guest molecules at the termini of the polymeric molecules allows the control of the co-polymer in situ through the application of external stimuli, as described above. The properties of the co-polymer may, for example, revert to the properties of the homopolymer by removal of one of the guest molecules through application of the external stimulus, as described above.

In some embodiments, a supramolecular block co-polymer may be amphiphilic. An amphiphilic block co-polymer may comprise;
  one or more of units of a hydrophobic polymer having first CB[8] guest molecules at its termini; and,
  one or more units of a hydrophilic polymer having second CB[8] guest molecules at its termini,
  the units of the hydrophobic and hydrophilic polymer being non-covalently linked by ternary guest-host complexes comprising the first and second CB[8] guest molecules and a CB[8] molecule.

In some preferred embodiments, a population of amphiphilic block co-polymers is able to form a micelle or vesicle in aqueous solution i.e. the hydrophobic and hydrophilic regions of the co-polymer molecules can align to form a hydrophilic exterior and an hydrophobic interior.

Such amphiphilic block co-polymers may be useful as encapsulants. An encapsulant may comprise a plurality of amphiphilic block co-polymers;
  each amphiphilic block co-polymer comprising;
    one or more of units of a hydrophobic polymer having first CB[8] guest molecules at its termini; and,
    one or more units of a hydrophilic polymer having second CB[8] guest molecules at its termini,
    the units of the hydrophobic and hydrophilic polymer being non-covalently linked by ternary guest-host complexes comprising the first and second CB[8] guest molecules and a CB[8] molecule,
wherein said plurality of block co-polymers aggregate to form a micelle in aqueous solution.

Compounds may be encapsulated within the micelles or vesicles of the amphiphilic block co-polymers. A method of encapsulation may comprise;
  admixing in aqueous solution a compound for encapsulation and a plurality of amphiphilic block co-polymers
  each amphiphilic block co-polymer comprising one or more of units of a hydrophobic polymer having first CB[8] guest molecules at its termini; and,
  one or more units of a hydrophilic polymer having second CB[8] guest molecules at its termini,
  the units of the hydrophobic and hydrophilic polymer being non-covalently linked by ternary guest-host complexes comprising the first and second CB[8] guest molecules and a CB[8] molecule,
  such that the plurality of co-polymers form a micelle encapsulating the compound.

In some preferred embodiments, the hydrophilic polymer is PEG.

In some preferred embodiments, the hydrophobic polymer is polystyrene, polyisoprene or other hydrophobic polymer described above.

Amphiphilic co-polymers as described herein may be useful as drug delivery vehicles for delivering encapsulated therapeutic compounds to a target site. A vehicle for delivery of a therapeutic compound may comprise:
  a plurality of amphiphilic block co-polymers
    each amphiphilic block co-polymer comprising one or more of units of a hydrophobic polymer having first CB[8] guest molecules at its termini; and,
    one or more units of a hydrophilic polymer having second CB[8] guest molecules at its termini,
    the units of the hydrophobic and hydrophilic polymer being non-covalently linked by ternary guest-host complexes comprising the first and second CB[8] guest molecules and a CB[8] molecule,
    said plurality of co-polymers forming a micelle having an internal cavity, containing a therapeutic compound for delivery.

Another aspect of the invention provides a vehicle for delivery of a therapeutic compound as described above for use in a method of treatment of the human or animal body, in particular for use in a method of delivering the therapeutic compound to a target site in an individual as described herein. This may be useful in the treatment of any disease condition for which administration of the therapeutic compound is beneficial.

A method of producing a vehicle for delivery of a therapeutic compound may comprise:
  admixing in aqueous solution a therapeutic compound and a plurality of amphiphilic block co-polymers
  each amphiphilic block co-polymer comprising one or more of units of a hydrophobic polymer having first CB[8] guest molecules at its termini; and,
  one or more units of a hydrophilic polymer having second CB[8] guest molecules at its termini,
  the units of the hydrophobic and hydrophilic polymer being non-covalently linked by ternary guest-host complexes comprising the first and second CB[8] guest molecules and a CB[8] molecule,
  such that the plurality of co-polymers form a micelle encapsulating the therapeutic compound.

The supramolecular polymers and assemblies described herein are responsive to external stimuli. This may allow the delivery of therapeutic compounds to a target site in an individual. A method of delivering a therapeutic compound to a target site in an individual may comprise:
  administering to the individual one or more micelles comprising a therapeutic compound encapsulated by a plurality of amphiphilic block co-polymers
  each amphiphilic block co-polymer comprising;
    one or more of units of a hydrophobic polymer having first CB[8] guest molecules at its termini; and,
    one or more units of a hydrophilic polymer having second CB[8] guest molecules at its termini,
    the units of the hydrophobic and hydrophilic polymer being non-covalently linked by ternary guest-host complexes comprising the first and second CB[8] guest molecules and a CB[8] molecule,
  stimulating micelles at the target site to release the first and/or the second CB[8] guest molecule from the ternary guest-host complexes, thereby disrupting the micelle and releasing the therapeutic agent at the therapeutic site.

The release of the therapeutic compound at the target site may be stimulated by applying a suitable external stimulus, such as electrochemical potential, pH, light, or oxygen. Changes in temperature at the target site may be used to release the therapeutic compound. The nature of the stimulus which is applied will depend on the CB[8] guest molecules which are employed, as described above.

While it is possible for supramolecular polymers, vehicles and encapsulants comprising a therapeutic compound as described herein to be administered alone, it is preferable to present them as pharmaceutical compositions (e.g. formulations) comprising the supramolecular polymer, vehicle or encapsulant defined above, together with one or more pharmaceutically acceptable carriers, adjuvants, excipients, diluents, fillers, buffers, stabilisers, preservatives, lubricants, or other materials well known to those skilled in the art. Optionally, other therapeutic or prophylactic agents may be included.

Thus, the present invention further provides pharmaceutical compositions, as defined above, and methods of making a pharmaceutical composition comprising admixing a supramolecular polymer, vehicle or encapsulant as described herein, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, Remington's Pharmaceutical Sciences, 18th edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

Formulations suitable for parenteral administration (e.g. by injection, including cutaneous, subcutaneous, intramuscular, intravenous and intradermal), include aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous sterile suspensions which may include suspending agents and thickening agents. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

It will be appreciated that appropriate dosages of the supramolecular polymer, encapsulant or vehicle comprising the therapeutic compound can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

Other aspects of the invention relate to the use of supramolecular polymers as described herein in systems for template directed self-assembly. For example, one of the guest molecules may be immobilised onto a solid surface. Supramolecular polymers and assemblies may be produced by successive interactions with material linkages/patterning (2D and 3D surfaces).

In other aspects of the invention, supramolecular polymers as described herein may be used in methods for the preparation of modified or extended polymer molecules. Specifically, CB[8] may act as a catalyst that holds together, non-covalently, a polymeric molecule and an attachment compound. Whilst the polymeric molecule and the attachment compound are held together with CB[8] as a supramolecular assembly, a covalent bond may be formed between the polymeric molecule and the attachment compound. The product may then be released from CB[8] using the techniques described herein. The covalent bond may be formed without the need for reagents, for example the polymeric molecule and the attachment compound may be activated for coupling, or the reaction may be a cycloaddition reaction, such as a Diels-Alder reaction, which may be initiated by heat or light. Alternatively, chemical coupling or bond forming reagents may be used.

The selectivity of the interaction of CB[8] with guest molecules allows for the purification of target molecules from samples. A method of purifying a target molecule from a sample may comprise;
  providing a sample comprising a target molecule linked to a first CB[8] guest molecule,
  contacting the sample with an immobilised first complex comprising a CB[8] molecule and a second CB[8] guest molecule such that the first CB[8] guest molecule interacts with the first complex to form a second complex comprising the CB[8] molecule, the first and second CB[8] guest molecules and the target molecule linked to the first CB[8] guest molecule,
  isolating the second complex and.
  releasing the first CB[8] guest molecule linked to the target molecule from the complex,
the target molecule being purified from the sample.

A sample may include any composition, mixture or extract which comprises the target molecule and other components or elements from which the target molecule needs to be purified.

The first complex may be immobilised, for example, by attachment to an insoluble support. The support may be in particulate or solid form and may include a plate, slide, a test tube, beads, a ball, a filter or a membrane. The first complex may, for example, be fixed to an insoluble support that is suitable for use in affinity chromatography. In some embodiments, first complex may be attached to the insoluble support through a binding member linked to the second CB[8] guest molecule. The binding member is fixed to the insoluble support and has the second CB[8] guest molecule at a free terminal. Suitable binding members and methods of attachment to insoluble supports are well known in the art. In some embodiments, the binding member may comprise a polymeric molecule, such as those polymeric molecules described. The polymeric molecule may be in particulate or solid form. In some embodiments, the CB[8] molecule may be fixed to a support.

In other aspects, there is provided a biomolecule, such as a polypeptide, linked to a CB[8] guest molecule. Where the biomolecule is a polypeptide, the CB[8] guest molecule and the polypeptide may be linked through a thioether-containing linkage formed from a cysteine thiol of the polypeptide and a maleimide group connected to the guest molecule.

The CB[8] guest molecule of the biomolecule may be used as a handle to "capture" the biomolecule in the form of a supramolecular polymer. Thus, an attachment compound linked to a CB[8] guest molecule or a polymeric molecule linked to a CB[8] guest molecule may be used together with CB[8] to form a ternary host-guest complex, wherein said complex non-covalently links the biomolecule and the attachment compound in a supramolecular polymer. Together, CB[8] with either the attachment compound or the polymeric molecule may be regarded as a hook to fish out a labelled biomolecule from a mixture or an aqueous solution.

Other aspects of the invention relate to the use of supramolecular polymers as described herein in microelectronics and/or optoelectronics. For example, an AABB type diblock polymer with acceptor and donor blocks in a defined architecture may be useful as an active component in a photovoltaic or other optoelectronic device.

Various further aspects and embodiments of the present invention will be apparent to those skilled in the art in view of the present disclosure. All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures and tables described below.

Figure 11:
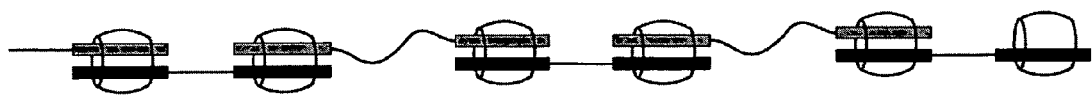
Figure 11:
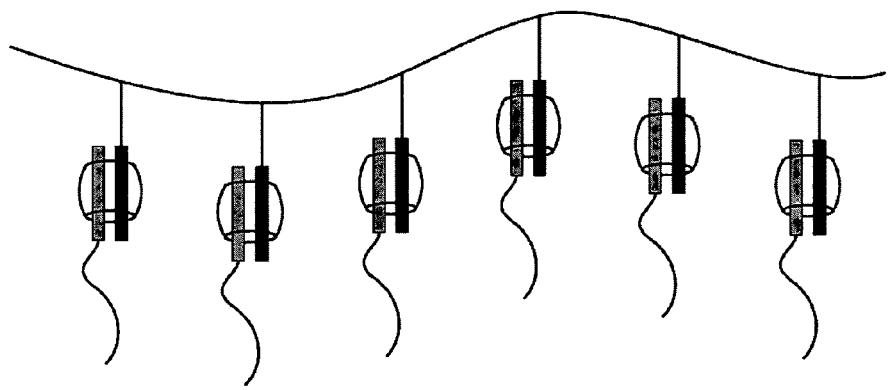

FIG. 11 is a schematic of (a) a portion of a main-chain supramolecular polymer according to an embodiment of the invention; and (b) a side-chain supramolecular polymer according to an embodiment of the invention. The main chain polymer comprises an alternating series of first and second polymers, each having CB[8] guest molecules at their termini. The side-chain supramolecular polymer comprises a first polymer having a plurality of CB[8] guest molecules at branches of the polymer, and a plurality of second polymers each having a CB[8] guest molecule at a terminal. In each system, the CB[8] guest molecules interact with a cucurbit[8]uril (CB[8]) molecule to form a ternary host-guest complex linking the polymers.

Figure 12:
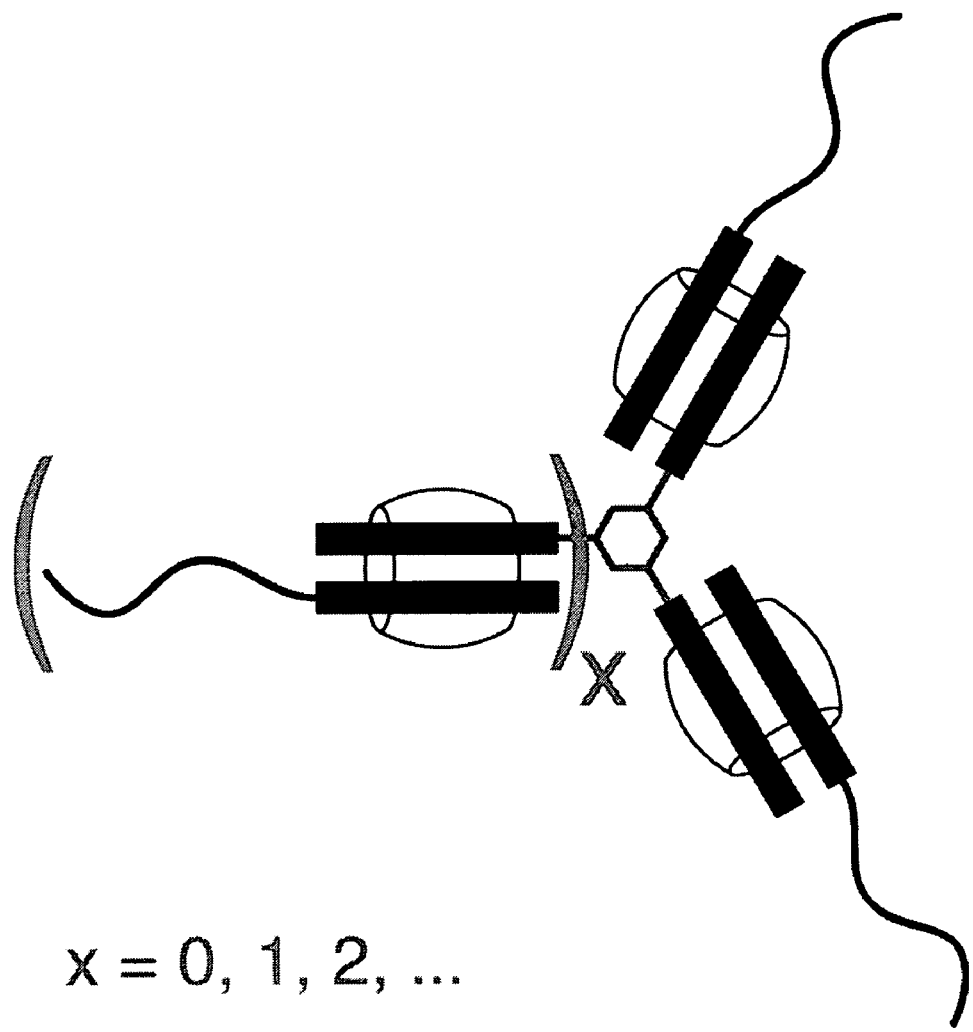

FIG. 12 is a schematic of a star-type supramolecular polymer according to an embodiment of the invention. The supramolecular polymer comprises a central linker having two or more CB[8] guest molecules, and a plurality of polymers each having a CB[8] guest molecule at a terminal. The CB[8] guest molecules interact with a cucurbit[8]uril (CB[8]) molecule to form a ternary host-guest complex linking the polymers to the central linker.

Figure 13:
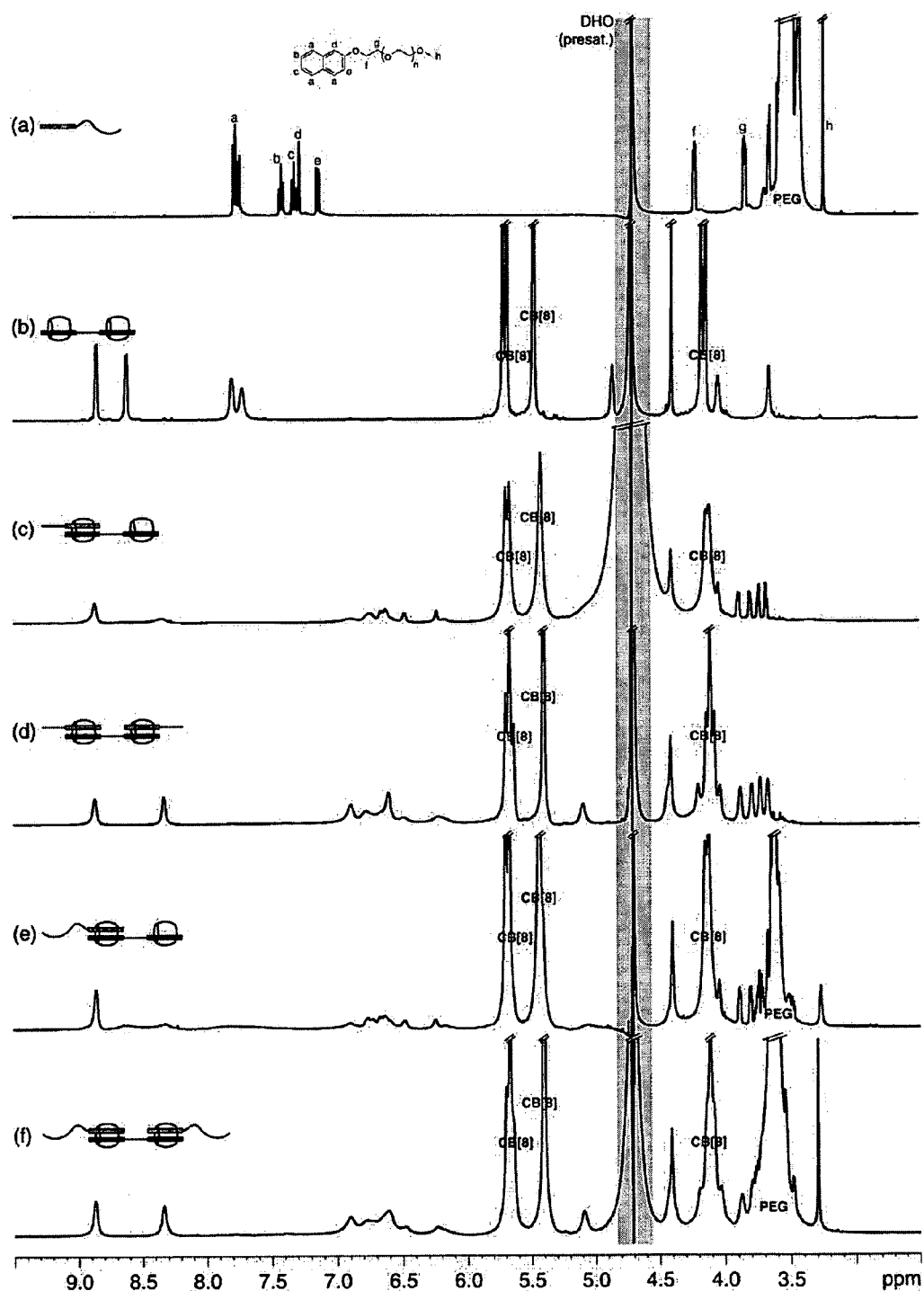

FIG. 13 shows the $^1$H NMR spectra (500 MHz) in $D_2O$ of NpPEG (a) and of the complexes CB[8]:MVdimer 2:1 (b), CB[8]: MVdimer:NpTEG 2:1:1 (c), CB[8]:MVdimer:NpTEG 2:1:2 (d), CB[8]:MVdimer:NpPEG 2:1:1 (e) as well as CB[8]:MVdimer:NpPEG 2:1:2 (f).

EXPERIMENTS

EXAMPLE 1

Supramolecular Block Copolymers with CB[8] in Water

Bromo-poly(ethylene glycol) monomethyl ether (6)

Bromination of poly(ethylene glycol) was performed for several different molecular weights. Typically 10 mmol of polymer was dissolved in toluene under nitrogen atmosphere with slight heating. Then, triethylamine (2.8 mL, 20 mmol) was added followed by careful drop-wise injection of thionyl bromide (1.23 mL, 16 mmol). The mixture was refluxed for 20 minutes and any precipitate filtered off. The flask was stirred overnight and the solvent reduced to about 100 mL by rotary evaporation. The sample was then freeze-dried under high vacuum and precipitated in ether to obtain the product in high yield (98%).

2-Naphthoxy-poly(ethylene glycol) monomethyl ether (7)

Naphthol terminal PEGs were successfully obtained from both tosylated PEG (4) as well as brominated PEG (6). A 50 mL RB flask was charged with activated poly(ethylene glycol) (0.5 mmol) of various molecular weight, 2-Naphthol (2.5 mmol, 0.36 g), potassium carbonate (0.48 g, 3.5 mmol) and acetonitrile (20 mL). The mixture was refluxed for up to five days under nitrogen atmosphere and then precipitated in cold ether. The precipitate was dried by vacuum filtration, dissolved in dichloromethane (20 mL), washed twice with brine and precipitated again into ether (200 mL) to obtain the pure product (78%).

Methyl viologen terminal poly(ethylene glycol) monomethyl ether (8)

Typically 5 mmol of 1 was dissolved with heating in dry acetonitrile (100 mL) under nitrogen atmosphere. Then, bromo-poly(ethylene glycol) monomethyl ether of desired molecular weight (1 mmol) was added and the mixture heated at reflux for 7 days. The solvent was removed by rotary evaporation and the crude product was dissolved in dichloromethane (15 mL) and precipitated in ether. The product was then subjected to dialysis in water using 500 or 1000 MWCO Float-A-Lyzer membranes. Finally freeze-drying off the water yielded the purified product as a fluffy yellowish solid (56%).

Tosylated 1,4-polyisoprene

A 50 mL RB flask was charged with polyisoprene (3.0 g, 0.3 mmol), pyridine (0.5 mL) and dichloromethane (20 mL). p-Toluenesulfonyl chloride (0.57 g, 3 mmol) was added and the reaction was stirred for 48 hours under nitrogen atmosphere. It was precipitated in cold methanol, collected by filtration and dissolved in dichloromethane (30 mL). It was subsequently washed twice with 3M HCl, then twice with water and finally with brine. The product was dried over $Na_2SO_4$ and the solvent was removed in vacuo to yield the tosylated polymer (2.5 g, 85%). 1H NMR (CDCl$_3$): δ=7.82 (d, 2H), 7.37 (d, 2H), 5.16 (m, (n-x)*1H), 4.75 (m, x*1H), 4.0 (m, 2H), 2.48 (s, 3H), 2.1 (m, n*4H), 1.73 (m, n*3H), 1.50 (m, 1H), 1.42 (m, 2H), 0.90 (m, 6H) ppm.

2-Naphthol Terminated Polyisoprene

Tosylated polyisoprene (0.4 g, 0.04 mmol) and 2-naphthol (144 mg, 1 mmol) were dissolved in dioxane (10 mL) in a 50 mL RB flask. Potassium carbonate (276 mg, 2 mmol) were added and the reaction mixture stirred at 80° C. for 5 days. Subsequently it is precipitated twice into a stirred dry ice/methanol mixture (200 mL) to obtain the product in 87% yield. $^1$H NMR (CDCl$_3$): δ=8.10–7.0 (m, 7H), 5.16 (m, (n-x)*1H), 4.75 (m, x*1H), 4.1 (m, 2H), 2.1 (m, n*4H), 1.73 (m, n*3H), 1.50 (m, 1H), 1.42 (m, 2H), 0.90 (m, 6H) ppm.

Results

Figure 2:
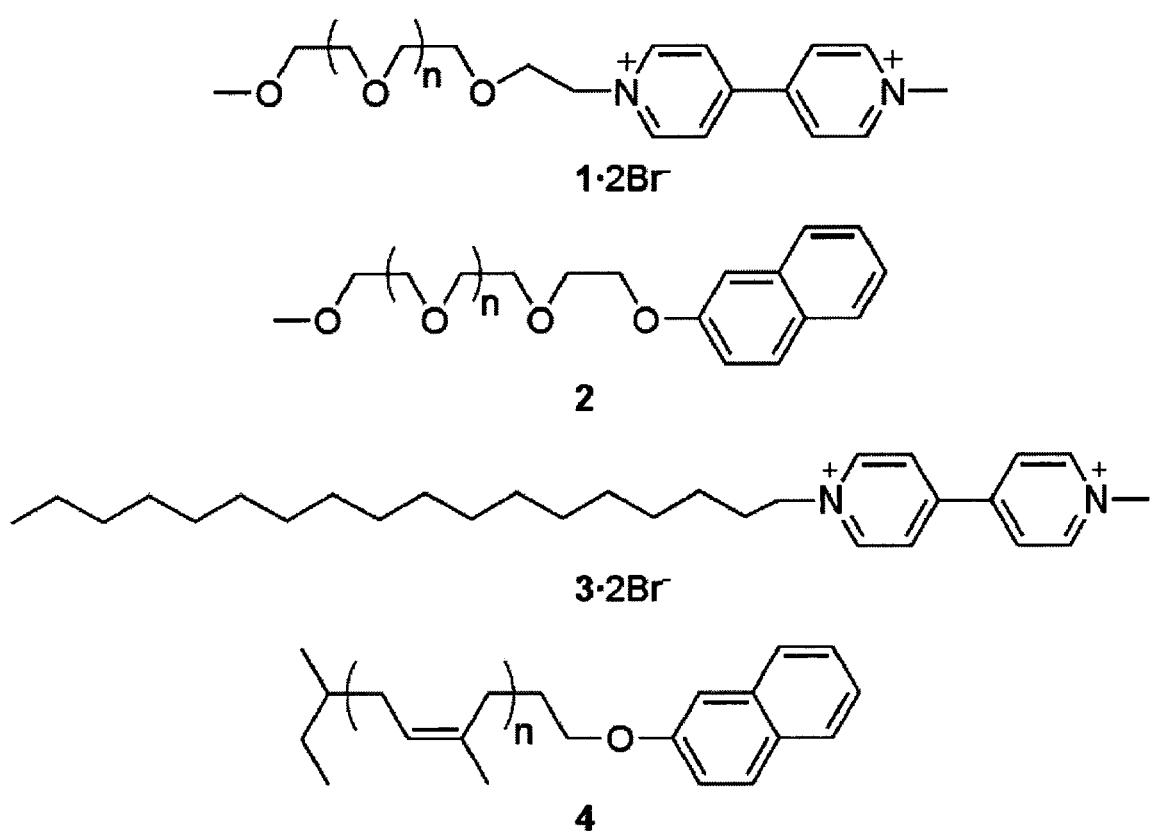
FIG. 2 shows end-group functional polymers prepared based on monofunctional poly(ethylene glycol) monomethyl ethers (1, 2) and cis-1,4-polyisoprene (4). Octadecyl methyl viologen (3) was prepared as a small molecule hydrophobic guest.
Figure 3:
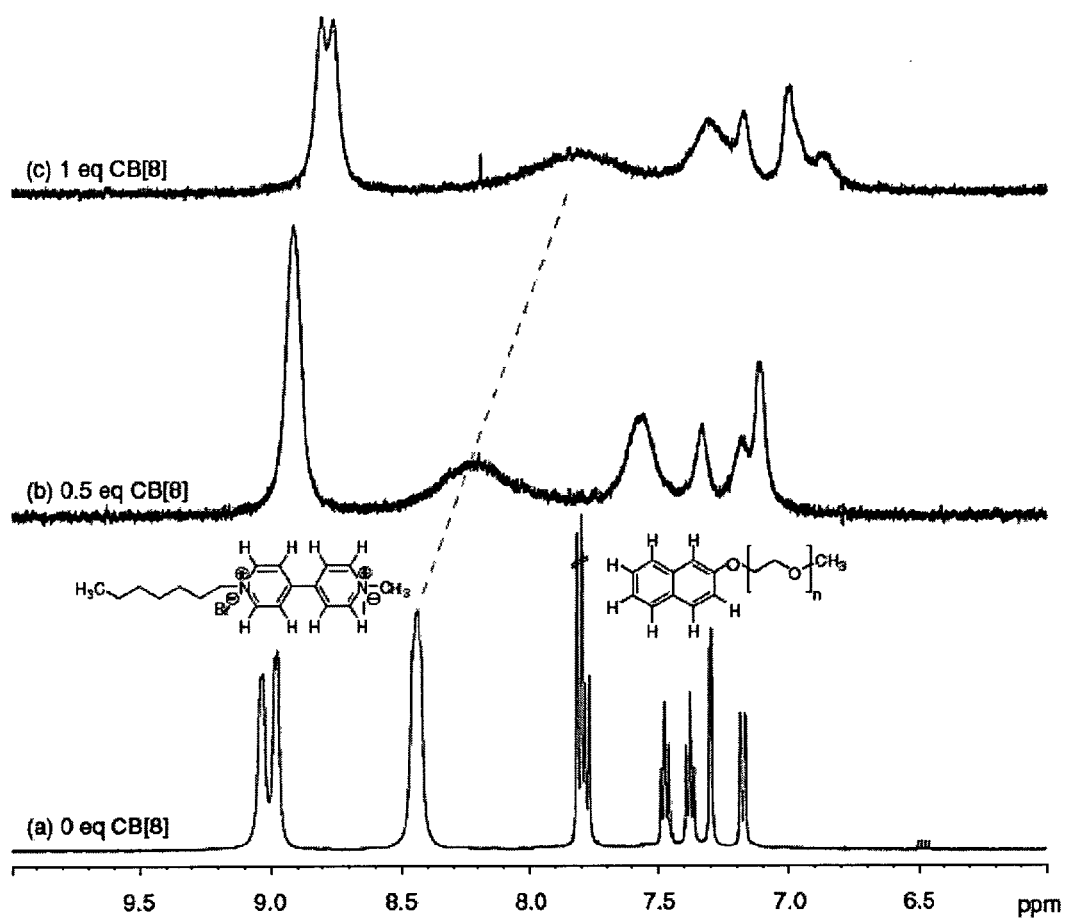
FIG. 3 shows NMR results which show complex formation (a) shows PEG or small molecule-PEG conjugate overlay and (b) shows polyisoprene system.

Here we report our first results of utilizing CB[8] as a linking unit for polymeric systems. In a first step, linear polymers were prepared that contained terminal groups such as 2-naphthol and methyl viologen derivatives for selective encapsulation by CB[8]. The polymers used are poly(ethylene glycol) (PEG) and cis-1,4-polyisoprene (PI). Their combination allows for the formation of an amphiphilic block copolymer that can be expected to exhibit secondary nanostructures in solution (FIG. 2).[36] Treatment of a 5000 molecular weight methyl viologen terminated poly(ethylene glycol) monomethyl ether (MV-PEG5k) with one equivalent of CB[8] in $D_2O$ resulted in an upfield shift and broadening of the aromatic protons on the viologen moiety. This result is indicative of complexation with a methyl viologen guest inside the cavity of the CB[8] host. Clearly, the steric bulk of the MV-PEG$_{5k}$ was not prohibitive in the host-guest molecular recognition. As CB[8] is uniquely poised in its ability to simultaneously bind two guests forming a 1:1:1 ternary complex, the MV-PEG$_{5k}$⊂CB[8] complex was exposed to an aqueous solution of 2-naphthol. Formation of the ternary complex was confirmed by both $^1$H NMR exhibiting a further upfield shift and broadening as well as UV/vis where a strong CT band (λmax=4xx nm with a shoulder at 5xx nm) was observed. All of these observations are in keeping with their small molecular analogues.[29]

To investigate CB[8] binding of two polymeric guests, a 5000 molecular weight 2-naphthol terminated poly(ethylene glycol) monomethyl ether (Np-PEG$_{5k}$) was added to a solution of MV-PEG$_{5k}$⊂CB[8] in $D_2O$.

Figure 1:
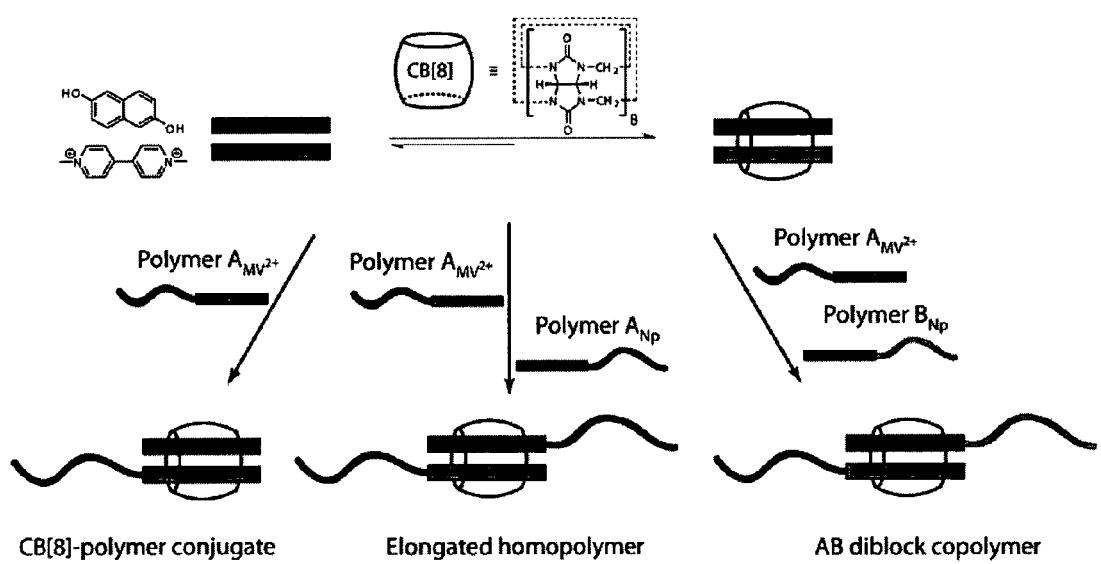
FIG. 1 shows examples of reaction schemes according to embodiments of the invention.
Figure 4:
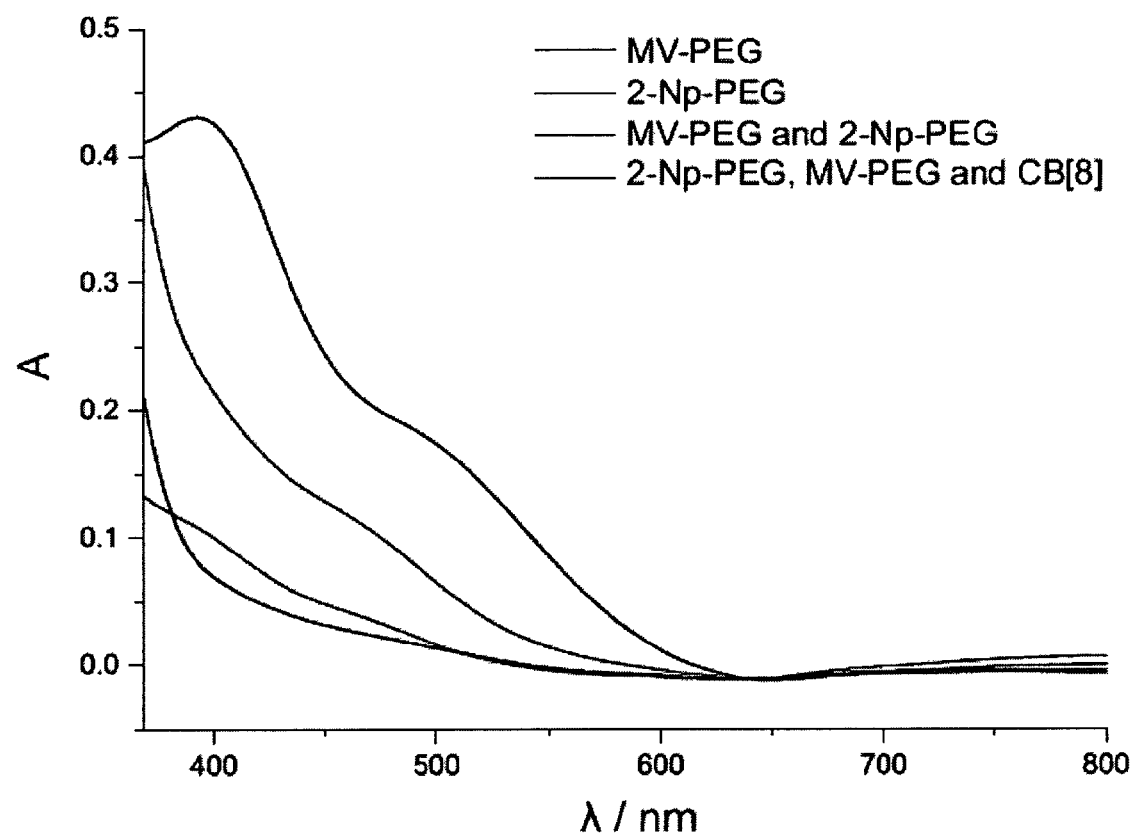
FIG. 4 shows UV/Vis spectra in water of $MV^{2+}$-PEG, 2-Np-PEG, $MV^{2+}$-PEG & 2-Np-PEG and PEG-$MV^{2+}$-CB[8]-2-Np-PEG complex showing the formation of a charge transfer band in the presence of CB[8].

1H NMR was again indicative of complex formation. UV/vis spectra of MV-PEG5k, Np-PEG$_{5k}$ and CB[8] (FIG. 4) illustrate that solutions of both MV-PEG$_{5k}$ and Np-PEG$_{5k}$ guests alone have no appreciable absorption beyond 400 nm. When both solutions are mixed together, a slight increase in UV/vis absorption results signifying a weak CT interaction of the respective polymer end groups. In the presence of CB[8] this CT interaction becomes strong and the emergence of a charge transfer band (at λmax=550 nm) provides evidence for complexation. This demonstrates that polymer chains can be extended using CB[8] as a linking unit as depicted in FIG. 1.

Ubbelohde viscometry measurements were performed to probe changes in solution viscosity upon complexation. [Clearly, polymer elongation was taking place.] Viologen 3 was synthesized with a C18 (octadecyl) chain. This only sparingly water-soluble guest can be pulled into water by Np-PEG$_{5k}$ in the presence of CB[8] as observed by $^1$H NMR.

Addition of CB[8] to a solution of Np-PEG$_{5k}$ and 3 led to complexation and an increase in solubility for the guest. Following the observation that the solubility of hydrophobic compounds in water can be increased by CB[8] complexation with PEG guests, it was envisioned that an amphiphilic diblock copolymer on the basis of CB[8] could be created.

Thus, 10000 molecular weight 2-naphthol terminated cis-1,4-polyisoprene (Np-PI$_{10k}$) was prepared and added to a solution of MV-PEG$_{5k}$⊂CB[8] in D$_2$O followed by rigorous shaking for several hours. Initial $^1$H NMR of the filtered D$_2$O solutions results indicated that a CT complex was indeed formed.

Figure 5:
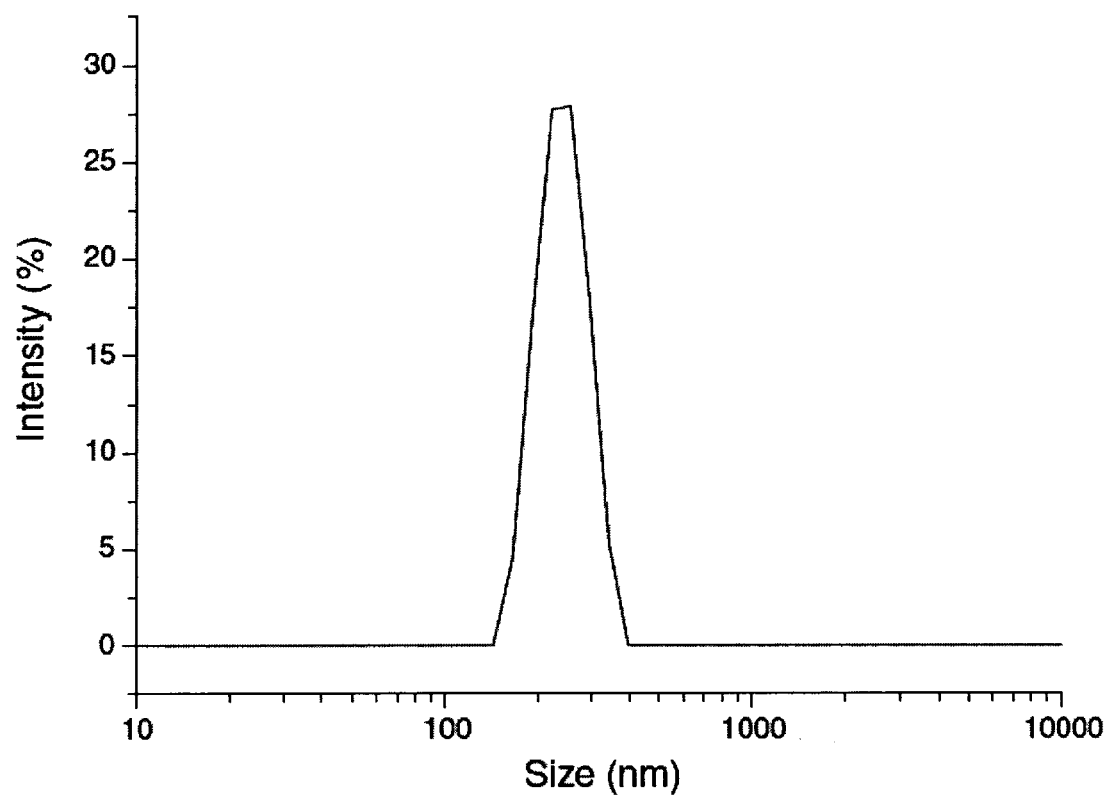
FIG. 5 shows dynamic light scattering results of a Np-$PI_{10k}$: MV-$PEG_{5k}$:CB[8] (1:1:1) system indicated the formation of a secondary solution structure with an average diameter of around 200 nm in water.
Figure 6:
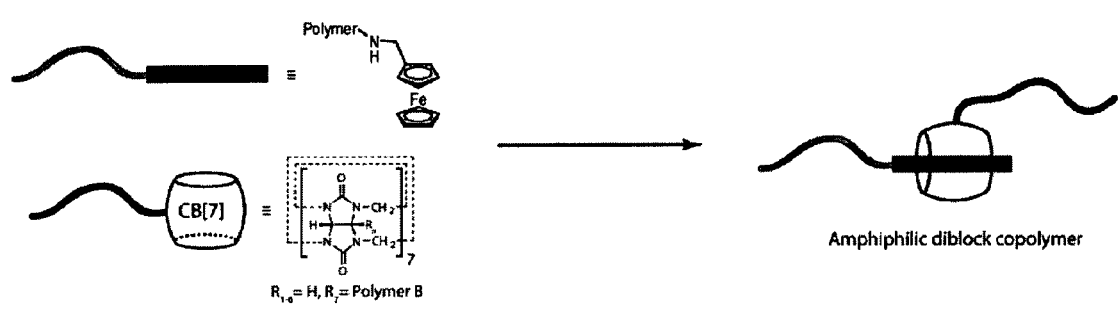
FIG. 6 shows examples of reaction schemes according to other embodiments of the invention.

The proton signals from the PI block are invisible, which provides indication that they are buried in an immobile and nonsolvated phase such as a micellar core. Further evidence for the formation of a secondary solution structure was provided by dynamic light scattering (FIG. 5).

Cucurbit[8]uril was shown to be capable of binding to polymers in aqueous media. Its capability to selectively bind two guest molecules has been exploited in the design of new polymeric blocks. Polymer-small molecule conjugates, elongated polymer chains and diblock copolymers were all synthesized showing the versatility of this approach. In comparison to existing strategies for non-covalent polymer preparation, CB[8] offers a both strong and dynamic binding profile in aqueous environments.

EXAMPLE 2

Discrete Multi-Component Complexes with CB[8]

CB[8] and NpPEG (2000 g/moL) were prepared according to the procedures described by Kim et al and Rauwald et al.[40, 41]

Synthesis of (MVdimer.4Br$^-$)

A 500 mL RB flask was charged with mBIPY (3.6 g, 12 mmol), 1,2-bis(2-bromoethoxy)ethane (0.8 g, 3 mmol) and acetonitrile (200 mL). The reaction mixture was heated to reflux for 48 h under a nitrogen atmosphere. A red precipitate was collected and dissolved in the minimum volume of H$_2$0 and a concentrated aqueous solution of NH$_4$ PF$_6$ was added until no further precipitation was observed. The precipitate was filtered off, washed with water and recrystallized from water to give pure MVdimer.4 PF$^-_6$. The counterions were exchanged to Br$^-$ using tetraoctylammonium bromide to yield MVdimer.4Br$^-$ as a yellow solid (0.55 g, 24%). $^1$H NMR (D$_2$O):=9.06 (d, 4H), 9.00 (d, 4H), 8.51 (d, 4H), 8.47 (d, 4H), 4.86 (t, 4H), 4.46 (s, 6H), 4.04 (t, 4H), 3.64 (s, 4H) ppm. 1-Methyl-4,4'-bipyridinium iodide (mBIPY): A 500 mL RB flask was charged with 4,4'-bipyridine (10.0 g, 64 mmol) in 150 mL dichloromethane. Methyl iodide (5.0 mL, 81 mmol) in dichloromethane (50 mL) was added drop-wise to the stirred flask. The mixture was refluxed for 1 hour and left to cool with stirring. The yellow product was filtered off, purified by recrystallization from methanol and finally washed with ether (15.44 g, 81%). $^1$H NMR (d$_3$-MeCN):= 8.84 (d, 2H), 8.79 (d, 2H), 8.32 (d, 2H), 7.80 (d, 2H), 4.35 (s, 3H) ppm.

Synthesis of tri(ethylene glycol) 2-naphthyl ether (NpTEG)

2-Naphthol (14.4 g, 0.1 mol), potassium hydroxide (5.6 g, 0.1 mol) and 2-(2-(2-Chloroethoxy)ethoxy)ethanol (16.8 g, 0.1 mol) were dissolved in 100 mL butanol and refluxed for 16 h. The mixture was then filtered and the solvent removed under vacuum. The product was then isolated by column chromatography (16.1 g, 58%). $^1$H NMR (d6-DMSO):=7.82 (m, 3H), 7.46 (t, 1H), 7.35 (t, 1H), 7.33 (s, 1H), 7.18 (d, 1H), 4.57 (t, 1H), 4.22 (t, 2H), 3.82 (t, 2H), 3.63 (m, 2H), 3.57 (m, 2H), 3.50 (m, 2H), 3.45 (t, 2H) ppm.

Nano-electrospray mass spectra were recorded on a LCT MS (Micromass, UK) equipped with nanoflow Z-spray source. Data were analyzed using Masslynx 4.0 software (Micromass, UK). The spectra were obtained with the following parameters: needle voltage=1.5 kV, skimmer cone voltage=10-30 V and skimmer offset=5 V. It should be noted that absolute intensity of peaks in electrospray spectra is dependent on the ionization efficiency of the species. It is valid, however, to make relative comparisons between the intensity of the four host-guest complexes.

Results

Figure 7:
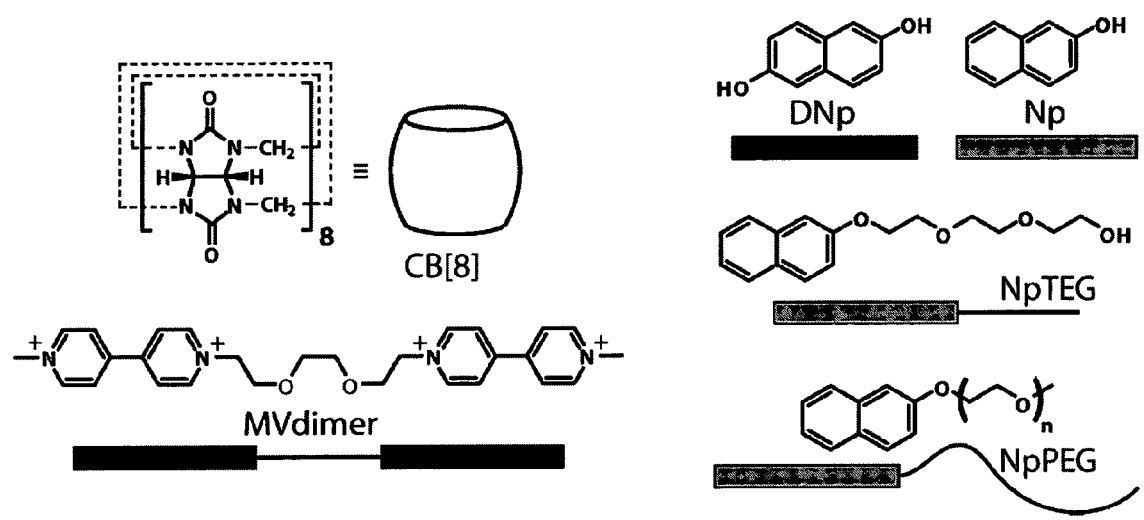
FIG. 7 shows the structures of CB[8], MVdimer, DNp, Np, NpTEG and NpPEG for use in certain embodiments of the present invention.

Here the formation of modular, multi-component, host-guest complexes is described where stoichiometry dictates the final architecture. By controlling the stoichiometry of the different subunits (see FIG. 7) in aqueous solution, quantitative self-assembly to the predicted and desired architecture is achieved. This strategy is extended to the preparation of functional polymeric assemblies of greater size and complexity in aqueous solution, including ABA triblock copolymer structures.

The key, core component of this system is a viologen dimer (MVdimer) which is composed of two methyl-4,4'-bipyridinium units connected by a flexible triethyleneglycol (TEG) linker. When MVdimer is mixed with different ratios of CB[8] and naphthol derivatives, such as 2,6-dihydroxynaphthalene (DNp), 2-naphthol (Np), tri(ethylene glycol) 2-naphthyl ether (NpTEG) or a 2,000 gmol$^{-1}$ 2-naphthoxy-terminated poly(ethyleneglycol) monomethyl ether (NpPEG), a variety of predetermined self-assembled architectures may be obtained. These architectures were analysed by $^1$H NMR spectroscopy and nano-electrospray mass spectrometry (MS). The latter technique has recently proven to be highly successful in investigating intricate host-guest dendritic assemblies, as well as binary host-guest mixtures with CB[6] and CB[7].[42, 43]

Figure 8:
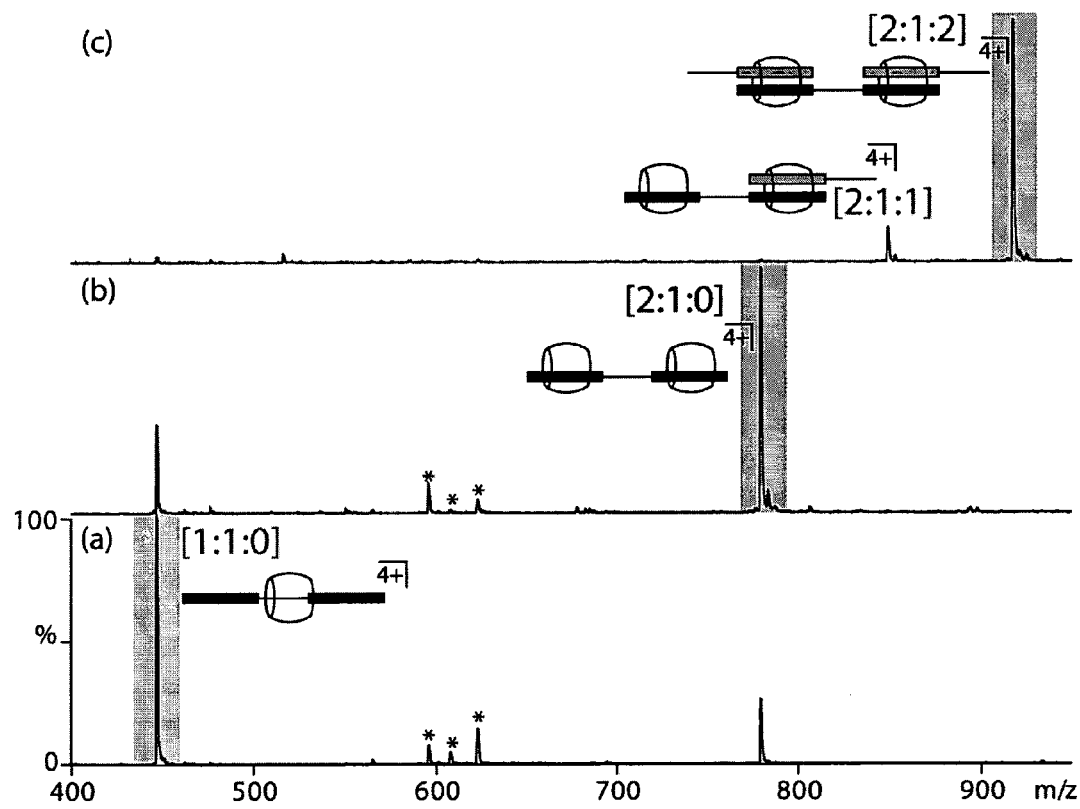
FIG. 8 shows mass spectra of MVdimer with one equiv of CB[8] (a), two equiv of CB[8] (b), and two equiv of CB[8] and two equiv of NpTEG (c). The peaks marked with an asterisk (*) correspond to $[1:1]^{3+}$ CB[8]:MVdimer inclusion complexes due to loss of $H^+$ or adducts with $Cl^-$ and $Br^-$ ions.

When a single equiv of CB[8] host is added to MVdimer in water, the main compound formed is the 1:1 CB[8]:MVdimer host-guest complex (FIG. 8a). This is revealed in the mass spectrum which shows a major peak at 447.0 m/z corresponding to the 4' charge state of this species. As observed previously with CB[8],[44] when two viologens are linked by a pure hydrocarbon chain, the host in the 1:1 complex is likely to encapsulate the linking chain as opposed to the viologen moiety. Evidence for this wheel-axle pseudo-rotaxane structure in the present system was obtained from $^1$H NMR measurements in D$_2$O. Upon addition of 1 equiv of CB[8], the signals for the linking TEG chain protons undergo a large upfield shift (nearly 1 ppm) relative to those of the free guest while the chemical shifts of MVdimer aromatic protons remain nearly unchanged (0.25 and 0.15 ppm downfield shift of β and β' protons and upfield shift of 0.5 ppm of α' protons). This clearly indicates that the CB[8] is mainly centered around the linker of MVdimer in solution. A second minor peak at 779.3 m/z is also observed on the MS spectrum and corresponds to the 4' charge state of the 2:1 CB[8]:MVdimer complex.

When a second equivalent of CB[8] is added to the previous solution, the predicted $[2:1]^{4+}$ host-guest complex is formed, which gives rise to the major peak in the MS at 779.3 m/z (FIG. 8b). The $^1$H NMR spectrum is now consistent with a 2:1 CB[8]:MVdimer host-guest complex with each viologen group being encapsulated by one CB[8] unit. Signals for the aromatic viologen protons are shifted upfield relative to the free guest, indicating that they are now located inside the cavity of CB[8]. Additionally, the signals from the TEG chain protons are shifted downfield relative to those in the 1:1 CB[8]:MVdimer complex, indicating they are no longer located inside the cavity of CB[8].

Upon addition of 1 equiv of DNp to a 1:1 CB[8]:MVdimer solution, MS signals of the 1:1:1 CB[8]:MVdimer:DNp ternary complex are barely discernible while the 2:1:1 and 2:1:2 CB[8]:MVdimer:DNp complexes are observed readily. This shows that the wheel-axle geometry of the 1:1 CB[8]:MVdimer complex initially formed is not favorable for the formation of a hetero-inclusion CT complex. Once a naphthol derivative (second guest) is added to the system, it is ensured that at least one, if not both viologen moieties must be encapsulated by a CB[8] host molecule so that the highly stable ternary complex can form.

Figure 9:
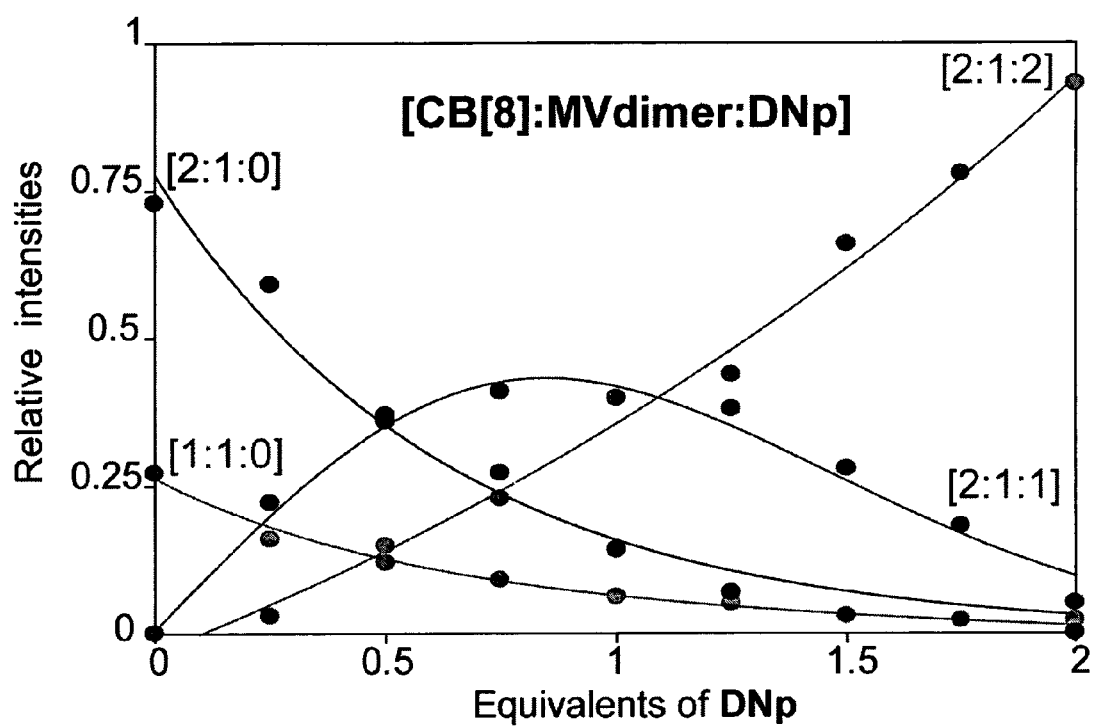
FIG. 9 shows the evolution of the relative intensities of the $4^+$ charge states of the different host-guest complexes formed upon stepwise addition of DNp to a 2:1 aqueous solution of CB[8]:MVdimer.

The stoichiometry of the host-guest complexes formed was monitored during a stepwise addition of DNp from 0 to 2 equiv to a 2:1 CB[8]:MVdimer solution (see stacked spectra in Figure S4, Supporting Information). The first CT host-guest complex formed is the four-component 2:1:1 [CB[8]:MVdimer:DNp]$^{4+}$ complex at 819.6 m/z. The second and final product of this titration is the five-component 2:1:2 CB[8]:MVdimer:DNp complex with its 4+ charge state appearing at 859.6 m/z. The relative intensities of the 4+ charge states of all the main species, i.e. the 1:1:0, 2:1:0, 2:1:1 and 2:1:2 host-guest complexes were determined for each titration step (FIG. 9).

At 0 equivalents of DNp, roughly 75% of the MS intensity can be attributed to the $[2:1:0]^{4+}$ complex, while some 1:1:0 complex is still observed at ~25% relative MS intensity, as previously described. Upon addition of DNp, the peaks attributed to $[1:1:0]^{4+}$ and $[2:1:0]^{4+}$ disappear progressively. The gradual disappearance of the 1:1:0 species does not lead to the formation of a detectable 1:1:1 host-guest complex, in which case a 4+ charge state should be observed at 487.0 m/z. The 2:1:1 CB[8]:MVdimer:DNp host-guest complex reaches its maximum intensity between 0.75 equiv and 1 equiv of DNp and beyond 1.25 equiv of DNp, the predominant product of this non-covalent assembly becomes the five-component 2:1:2 bis-ternary complex.

The pentameric complex can be readily modulated and the same structural motif can be obtained with other naphthol derivatives. For example, 2 equiv of Np were added to a 2:1 CB[8]:MVdimer solution which also leads to the unique formation of 2:1:2 CB[8]:MVdimer:Np inclusion complex observed in the MS as a main peak at 851.6 m/z assigned to its 4+ charge state. Furthermore, the architectural complexity may be increased through the addition of 2 equiv of an oligo (ethyleneglycol) functionalized 2-naphthol (NpTEG) to the 2:1 CB[8]:MVdimer solution which similarly produces the five-component host-guest complex, with the $[2:1:2]^{4+}$ complex at 917.5 m/z (FIG. 8c). Formation of the inclusion complex was also confirmed by $^1$H NMR in aqueous solution (see FIG. 13). Upon addition of 1 and 2 equiv of NpTEG to a 2:1 CB[8]:MVdimer solution, the aromatic protons signals of the MVdimer and the NpTEG exhibit an upfield shift and broadening, characteristic for this type of ternary complex inside a CB[8] cavity.[45]

Figure 10:
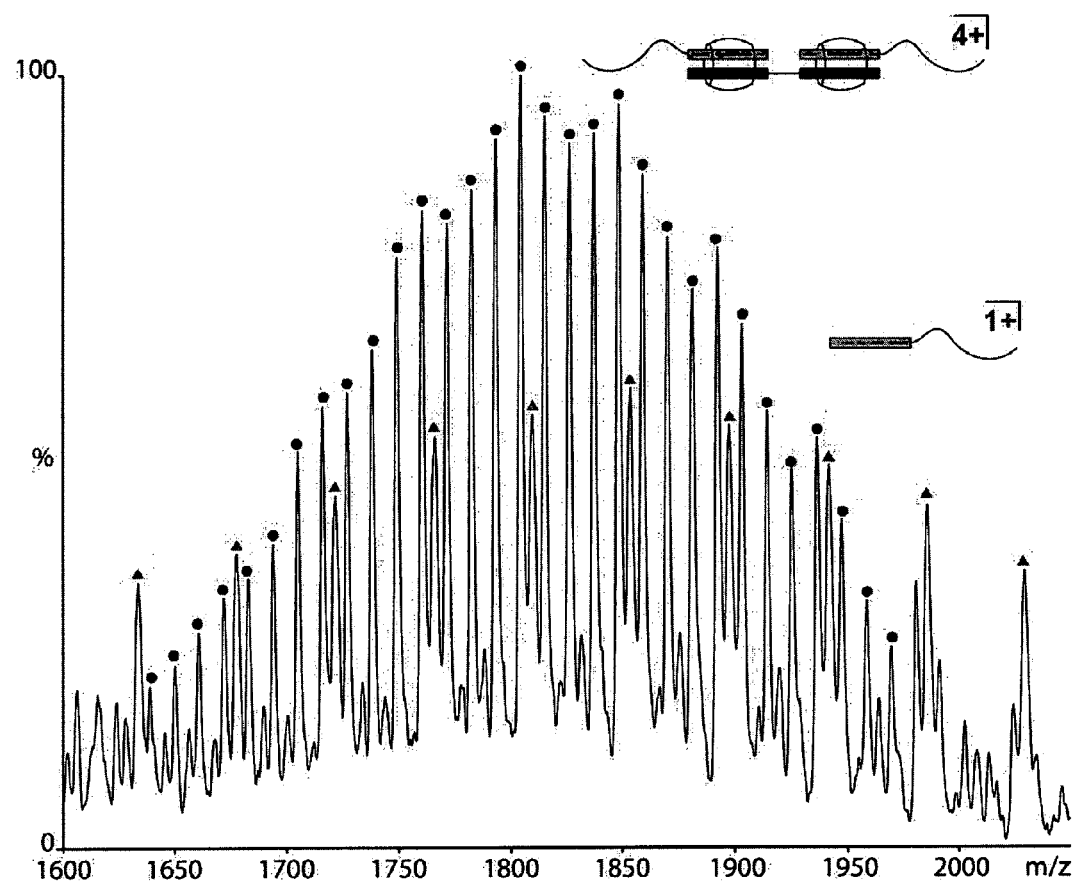
FIG. 10 shows the mass spectrum of the $4^+$ charge states of the pentameric ABA triblock copolymer complex of 2:1:2 CB[8]:MVdimer:NpPEG between 1,600-2,000 m/z (dots). The $1^+$ charge states ($Na^+$ adduct) of free NpPEG (triangles) are also found in this region.

The modularity described above indicated that such a system could be used to construct supramolecular ABA triblock copolymer structures. To investigate the formation of these polymeric assemblies, a 2000 gmol$^{-1}$ 2-naphthoxy-terminated poly(ethyleneglycol) monomethyl ether (NpPEG) was mixed with a 2:1 solution of CB[8]:MVdimer. The resulting assembly was investigated by nano-ESI-MS. Two polymeric distributions were observed in the mass spectrum, which can be assigned to the ABA triblock copolymer assembly in its 4$^+$ (~1600-2000 m/z, FIG. 10) and 5$^+$ (~1400-1600 m/z, Na adduct) charge states, confirming unambiguously the formation of the triblock copolymer assembly. Stepwise formation of the 2:1:1 and 2:1:2 CB[8]:MVdimer:NpPEG complexes was also probed by $^1$H NMR spectroscopy, and both spectra are consistent with the formation of inclusion complexes. When compared to the CB[8]:MVdimer:NpTEG system, the same spectral shifts of the aromatic protons are observed. This indicates that ternary host-guest complex formation occurs even when the guest molecule is functionalized by a 2000 gmol$^{-1}$ PEG polymer.

References

[1] Brunsveld, L. et al Rev. 2001, 101, 4071-4098.
[2] Ligthart, G. et al Supramolecular Polymer Engineering. In Macromolecular Engineering Precise Synthesis, Materials Properties, Applications; Matyjaszewski, K.; Gnanou, Y.; Leibler, L., Eds.; Wiley VCH: 2007.
[3] Bosman, A. W. et al Materials Today 2004, 7, 34-39.
[4] Sijbesma, R. P. et al Science 1997, 278, 1601-1604.
[5] Archer, R. D. Coordination Chemistry Reviews 1993, 128, 49-68.
[6] Swiegers, G. F. et al Chem. Rev. 2000, 100, 3483-3538.
[7] Lehn, J. -M. et al PNAS 1987, 84, 2565-2569.
[8] Knapp, R. et al Macromolecules 1996, 29, 478-480.
[9] Schtte, M. et al. Angewandte Chemie International Edition 1998, 37,2891-2893.
[10] Lohmeijer, B. G. G. et al Angewandte Chemie International Edition 2002, 41, 3825-3829.
[11] Chen, B.; Sleiman, H. F. Macromolecules 2004, 37, 5866-5872.
[12] Zhou, G.; Harruna, I. I. Macromolecules 2005, 38, 4114-4123.
[13] Fustin, C. -A. et al Advanced Materials 2007, 19,1665-1673.
[14] Scherman, O. A. et al PNAS 2006, 103, 11850-11855.
[15] Yang, X. et al Angewandte Chemie International Edition 2004, 43, 6471-6474.
[16] Higley, M. N. et al Chemistry—A European Journal 2005, 11, 2946-2953.
[17] Yamauchi, K. et al J. Am. Chem. Soc. 2002, 124, 8599-8604.
[18] Binder, W. H. et al. Journal of Polymer Science Part A: Polymer Chemistry 2004, 42, 162-172.
[19] Sontjens, S. H. M. et al J. Am. Chem. Soc. 2000, 122, 7487-7493.
[20] Shimizu, L. S. Polymer International 2007, 56, 444-452.
[21] Behrend, R. et al Jutus Liebig's Ann. Chem. 1905, 339, 1-37.
[22] Freeman, W. A. et al. J. Am. Chem. Soc. 1981, 103, 7367-7368.

[23] Kim, J. et al J. Am. Chem. Soc. 2000, 122, 540-541.
[24] Lagona, J. et al Angewandte Chemie International Edition 2005, 44,4844-4870.
[25] Kim, H. -J. et al Angewandte Chemie International Edition 2001, 40, 1526-1529.
[26] Sindelar, V. et al Chemistry—A European Journal 2005, 11, 7054-7059.
[27] Bush, M. E. et al J. Am. Chem. Soc. 2005, 127, 14511-14517.
[28] Jeon, Y. J. et al Angewandte Chemie International Edition 2002, 41, 4474-4476.
[29] Jeon, W. S. et al Angewandte Chemie International Edition 2005, 44, 87-91.
[30] Ko, Y. H. et al J. Am. Chem. Soc. 2004, 126, 1932-1933.
[31] Kim, K. et al Chemical Communications 2004, 848-849
[32] Jeon, W. S. et al Angewandte Chemie International Edition 2003, 42, 4097-4100.
[33] Ko, Y. H. et al Chem. Commun. 2007, 1305-1315.
[34] Moon, K. et al. Angewandte Chemie International Edition 2004, 43, 5496-5499.
[35] Wang, W.; Kaifer, A. E. Angewandte Chemie International Edition 2006, 45, 7042-7046.
[36] Floudas, G. et al Macromolecules 2001, 34, 2947-2957.
[37] Hwang, I.; Baek, K.; Jung, M.; Kim, Y.; Park, K. M.; Lee, D. W.; Selvapalam, N.; Kim, K. *J. Am. Chem. Soc.* 2007, 129, 4170-4171.
[38] Sun, S.; Zhang, R.; Andersson, S.; Pan, J.; Akermark, B.; Sun, L. *Chem. Commun.* 2006, 4195-4197.
[39] Jon, S. Y.; Ko, Y. H.; Park, S. H.; Kim, H. -J.; Kim, K. *Chem. Commun.* 2001, 1938-1939.
[40] J. Kim, I. S. Jung, S. Y. Kim, E. Lee, J. K. Kang, S. Sakamoto, K. Yamaguchi, K. Kim, J. Am. Chem. Soc. 2000, 122(3), 540-541.
[41] U. Rauwald, O. A. Scherman, Angew. Chem. Int. Ed. 2008, 47(21), 3950-3953.
[42] M. Broeren, J. van Dongen, M. Pittelkow, J. Christensen, M. van Genderen, and E. Meijer, *Angew. Chem. Int. Ed.,* 2004, 43, 3557.
[43] I. Osaka, M. Kondou, N. Selvapalam, S. Samal, K. Kim, M. Rekharsky, Y. Inoue, and R. Arakawa, J. Mass Spectrom., 2006, 41, 202.
[44] W. Jeon, A. Ziganshina, J. Lee, Y. Ko, J. -K. Kang, C. Lee, and K. Kim, *Angew. Chem. Int. Ed.,* 2003, 42, 4097.
[45] H. -J. Kim, J. Heo, W. Jeon, E. Lee, J. Kim, S. Sakamoto, K. Yamaguchi, and K. Kim, *Angew. Chem. Int. Ed.,* 2001, 40, 1526.

The invention claimed is:
1. A supramolecular polymer comprising a first polymeric molecule linked to a first cucurbit[8]uril (CB[8]) guest molecule and an attachment compound linked to a second CB[8] guest molecule,
wherein:
the first and second CB[8] guest molecules form a ternary host-guest complex with a CB[8] molecule, or a variant or derivative thereof, which non-covalently links the first polymeric molecule and the attachment compound in a supramolecular polymer; and
the first polymeric molecule has 15 or more monomer units.
2. The supramolecular polymer according to claim 1, wherein the first polymeric molecule is a hydrophilic polymer.
3. The supramolecular polymer according to 1, wherein the first polymeric molecule is (i) a hydrophilic polymer selected from the group consisting of polyethylene glycol (PEG), polyvinyl pyrrolidone (PVP), hydroxypropyl methylcellulose (HPMC), polypropylene, polyvinyl alcohol, polyacrylamide and derivatives and copolymers thereof, or (ii) a polypeptide.
4. The supramolecular polymer according to claim 1, wherein the attachment compound is a small organic molecule or a second polymeric molecule.
5. The supramolecular polymer according to claim 1, wherein the attachment compound and/or the first polymeric molecule together with their respective guest molecules are releasable from the supramolecular polymer, optionally by application of an external stimulus.
6. A block co-polymer comprising either:
(I) a first polymeric molecule unit having 15 or more monomers, and having CB[8] guest molecules at its termini; and
(a) two units of a second polymeric molecule each having a CB[8] guest molecule at a terminal, or
(b) two units of a linker molecule each having a CB[8] guest molecule;
the units of the first and second polymeric molecule, or the units of the first polymeric molecule and the linker molecule, being non-covalently linked by ternary guest-host complexes comprising:
a CB[8] guest molecule on each unit, and
a CB[8] molecule, or a variant or derivative thereof;
or:
(II) two units of a first polymeric molecule each having 15 or more monomers, and each having a CB[8] guest molecule, or a variant or derivative thereof, at a terminal; and,
(a) a second polymeric molecule unit having CB[8] guest molecules at its termini, or
(b) a linker molecule unit having CB[8] guest molecules at its termini;
the units of the first and second polymeric molecule, or the units of the first polymeric molecule and the linker molecule, being non-covalently linked by ternary guest-host complexes comprising:
a CB[8] guest molecule on each unit,
and a CB[8] molecule, or a variant or derivative thereof.
7. The block co-polymer according to claim 6 wherein the first polymeric molecule is a hydrophilic polymer or a hydrophobic polymer, and the second polymeric molecule, where present, is a hydrophobic polymer or a hydrophilic polymer.
8. An encapsulant comprising a plurality of amphiphilic block co-polymers, each amphiphilic block co-polymer comprising:
one or more of units of a hydrophobic polymer having first CB[8] guest molecules at its termini; and,
one or more units of a hydrophilic polymer having second CB[8] guest molecules at its termini,
the units of the hydrophobic and hydrophilic polymer being non-covalently linked by ternary guest-host complexes comprising:
the first and second CB[8] guest molecules, and
a CB[8] molecule, or a variant or derivative thereof,
wherein said plurality of block co-polymers aggregate to form a micelle or a vesicle in aqueous solution, and at least one polymer unit has at least 15 monomers.
9. A vehicle for delivery of a therapeutic compound comprising:
a plurality of amphiphilic block co-polymers, each amphiphilic block co-polymer comprising:
one or more of units of a hydrophobic polymer having first CB[8] guest molecules at its termini; and
one or more units of a hydrophilic polymer having second CB[8] guest molecules at its termini, the units of the hydrophobic and hydrophilic polymer being non-covalently linked by ternary guest-host complexes comprising:
the first and second CB[8] guest molecules, and
a CB[8] molecule, or a variant or derivative thereof,
said plurality of co-polymers forming a micelle or vesicle, containing a therapeutic compound for delivery;
wherein at least one polymer unit has at least 15 monomers.

10. A method of producing a supramolecular polymer comprising:
providing a first polymeric molecule linked to a first CB[8] guest molecule and an attachment compound linked to a second CB[8] guest molecule,
allowing the first and second CB[8] guest molecules to interact with a CB[8] molecule, or a variant or derivative thereof, to form a ternary host-guest complex,
wherein said ternary complex non-covalently links the polymeric molecule and the attachment compound in a supramolecular polymer, and the first polymeric molecule has at least 15 monomers.

11. The method according to claim 10 wherein the first and second CB[8] guest molecules interact with the CB[8] molecule in aqueous solution.

12. The method according to claim 10, wherein the first polymeric molecule is a hydrophilic polymer.

13. The method according to claim 10, wherein the first polymeric molecule is (i) a hydrophilic polymer selected from the group consisting of polyethylene glycol (PEG), polyvinyl pyrrolidone (PVP), hydroxypropyl methylcellulose (HPMC), polypropylene, polyvinyl alcohol, polyacrylamide and derivatives and copolymers thereof, or (ii) a polypeptide.

14. The method according to claim 10, wherein the attachment compound is a small organic molecule or a second polymeric molecule.

15. The method according to claim 10, wherein the attachment compound and/or the first polymeric molecule together with their respective guest molecules are releasable from the supramolecular polymer, optionally by application of an external stimulus.

16. A method of increasing the solubility of a compound in aqueous solution comprising;
providing a hydrophilic polymer linked to a first CB[8] guest molecule and a compound linked to a second CB[8] guest molecule,
allowing the first and second CB[8] guest molecules to interact with a CB[8] molecule, or a variant or derivative thereof, to form a ternary complex,
said ternary complex non-covalently linking the hydrophilic polymer to the compound to form a supramolecular polymer which has increased solubility in aqueous solution relative to the unattached compound,
wherein the hydrophilic polymer has at least 15 monomers.

17. The method according to claim 16 wherein the hydrophilic polymer is selected from the group consisting of polyethylene glycol (PEG), polyvinyl pyrrolidone (PVP), hydroxypropyl methylcellulose (HPMC), polypropylene, polyvinyl alcohol, polyacrylamide and derivatives and copolymers thereof.

18. A method of treatment of the human or animal body, the method comprising administering to a subject a supramolecular polymer comprising a hydrophilic polymer linked to a first CB[8] guest molecule and a therapeutic compound linked to a second CB[8] guest molecule, wherein the first and second CB[8] guest molecules form a ternary complex with a CB[8] molecule, or a variant or derivative thereof, to form the supramolecular polymer comprising the hydrophilic polymer and the therapeutic compound, wherein the hydrophilic polymer has at least 15 monomers.

19. A method of producing a block co-polymer comprising either:
(I) providing a population of first polymeric molecules, each having at least 15 monomers and having CB[8] guest molecules at their termini and
(a) a population of second polymeric molecules having a CB[8] guest molecule at a terminal; or
(b) a population of linker molecules each having a CB[8] guest molecule, which interact with CB[8] molecules to form ternary guest-host complexes,
contacting the populations of (a) first and second polymeric molecules; or (b) first polymeric molecules and linker molecules, with a population of CB[8] molecules, or variants or derivatives thereof, such that the CB[8] guest molecules interact with the CB[8] molecules, or variants or derivatives thereof, to form ternary guest-host complexes,
thereby producing a block co-polymer comprising (a) a plurality of first and second polymeric molecules non-covalently linked together by said ternary complexes; or (b) a plurality of first polymeric molecules and linker molecules non-covalently linked together by said ternary complexes;
or:
(II) providing a population of first polymeric molecules, each having at least 15 monomers and each having a CB[8] guest molecule at a terminal and
(a) a population of second polymeric molecules each having CB[8] guest molecules at their termini; or
(b) a population of linker molecules each having CB[8] guest molecules at their termini,
contacting the populations of (a) first and second polymeric molecules; or (b) first polymeric molecules and linker molecules, with a population of CB[8] molecules, or variants or derivatives thereof, such that the CB[8] guest molecules interact with the CB[8] molecules, or variants or derivatives thereof, to form ternary guest-host complexes,
thereby producing a block co-polymer comprising (a) a plurality of first and second polymeric molecules non-covalently linked together by said ternary complexes; or (b) a plurality of first polymeric molecules and linker molecules non-covalently linked together by said ternary complexes.

20. The supramolecular polymer according to claim 1, wherein the CB[8] molecule, or the variant or derivative thereof, has 8 or more units.

21. The supramolecular polymer according to claim 1, wherein the first polymeric molecule has 100 or more monomer units.

22. The supramolecular polymer according to claim 1, wherein the first polymeric molecule has a molecular weight of greater than 2,000.

* * * * *